(12) United States Patent
Degtiar et al.

(10) Patent No.: US 10,272,244 B2
(45) Date of Patent: Apr. 30, 2019

(54) RETINAL IMPLANT FIXATION

(71) Applicant: NANO RETINA LTD, Herzeliya (IL)

(72) Inventors: Boris Degtiar, Modiin (IL); Rani Mendelewicz, Herzliya (IL); Yaakov Milstain, Zichron-Yaakov (IL); Yossi Gross, Mazor (IL); Dorit Raz Prag, Pardes Hanna-Karkur (IL); Matan Zehavi, Netanya (IL); David Rigler, Kadima-Tzoran (IL)

(73) Assignee: NANO RETINA LTD., Herzliya (IL)

( * ) Notice: Subject to any disclaimer, the term of this patent is extended or adjusted under 35 U.S.C. 154(b) by 0 days.

(21) Appl. No.: 15/342,746

(22) Filed: Nov. 3, 2016

(65) Prior Publication Data
US 2018/0117329 A1    May 3, 2018

(51) Int. Cl.
*A61N 1/05* (2006.01)
*A61N 1/36* (2006.01)
(Continued)

(52) U.S. Cl.
CPC ........ *A61N 1/36046* (2013.01); *A61F 9/0017* (2013.01); *A61N 1/0543* (2013.01); *A61N 1/375* (2013.01); *A61N 1/37205* (2013.01)

(58) Field of Classification Search
CPC .......................... A61N 1/0543; A61N 1/36046
See application file for complete search history.

(56) References Cited

U.S. PATENT DOCUMENTS

| 5,597,381 A | 1/1997 | Rizzo, III |
| 6,368,349 B1 | 4/2002 | Wyatt et al. |
| (Continued) | | |

FOREIGN PATENT DOCUMENTS

| WO | 02/091934 | 11/2002 |
| WO | 2010/089739 | 8/2010 |
| (Continued) | | |

OTHER PUBLICATIONS

An Office Action dated Apr. 27, 2018, which issued during the prosecution of U.S. Appl. No. 15/342,765.
(Continued)

*Primary Examiner* — Eric D. Bertram
(74) *Attorney, Agent, or Firm* — Sughrue Mion, PLLC

(57) ABSTRACT

Apparatus is provided including an implantable retinal stimulator, for implantation on a retina of an eye, and including (i) an electrode array including electrodes; (ii) a plurality of photosensors; and (iii) driving circuitry, configured to drive the electrodes to apply currents to the retina. The apparatus further includes an interface member disposed at an outer surface of the implantable retinal stimulator, e.g., a peripheral member surrounding at least a portion of the implantable retinal stimulator. The apparatus additionally includes a frame, (i) shaped and sized to couple to the peripheral member and to surround the implantable retinal stimulator at least in part, and (ii) shaped to define at least a first anchoring element receiving portion. An anchoring element is shaped and sized to be positioned in the anchoring element receiving portion and to penetrate scleral tissue of the subject. Other applications are also described.

16 Claims, 15 Drawing Sheets

(51) Int. Cl.
*A61F 9/00* (2006.01)
*A61N 1/372* (2006.01)
*A61N 1/375* (2006.01)

(56) References Cited

U.S. PATENT DOCUMENTS

| | | | |
|---|---|---|---|
| 8,150,526 B2 | 4/2012 | Gross | |
| 8,428,740 B2 | 4/2013 | Gefen | |
| 8,442,641 B2 | 5/2013 | Gross | |
| 8,571,669 B2 | 10/2013 | Liran et al. | |
| 8,706,243 B2 | 4/2014 | Gefen et al. | |
| 8,718,784 B2 | 5/2014 | Gefen et al. | |
| 9,192,464 B2 | 11/2015 | Liran et al. | |
| 9,192,772 B1 | 11/2015 | Tsukamoto et al. | |
| 9,198,753 B2 | 12/2015 | Gefen et al. | |
| 9,265,945 B2 | 2/2016 | Gross et al. | |
| 9,331,791 B2 | 5/2016 | Liran et al. | |
| 9,370,417 B2 | 6/2016 | Gefen | |
| 9,474,902 B2 | 10/2016 | Gefen et al. | |
| 9,566,191 B2 | 2/2017 | Gefen et al. | |
| 2003/0014089 A1* | 1/2003 | Chow | A61F 9/0017 607/54 |
| 2004/0039401 A1* | 2/2004 | Chow | A61F 9/007 606/129 |
| 2004/0054407 A1* | 3/2004 | Tashiro | A61N 1/36046 623/6.22 |
| 2004/0078064 A1* | 4/2004 | Suzuki | A61F 2/14 607/54 |
| 2005/0165409 A1* | 7/2005 | Eckmiller | A61F 9/007 606/107 |
| 2006/0116743 A1* | 6/2006 | Gibson | A61N 1/375 607/57 |
| 2006/0224212 A1* | 10/2006 | Kennedy | A61N 1/0543 607/54 |
| 2008/0288067 A1 | 11/2008 | Flood | |
| 2009/0216295 A1 | 8/2009 | Zrenner et al. | |
| 2012/0065704 A1 | 3/2012 | Kavasssery et al. | |
| 2012/0239126 A1 | 9/2012 | Zhou et al. | |
| 2012/0259410 A1 | 10/2012 | Gefen et al. | |
| 2014/0046418 A1 | 2/2014 | Williams et al. | |
| 2014/0143559 A1 | 5/2014 | Gefen et al. | |
| 2015/0342723 A1 | 12/2015 | Abramson et al. | |
| 2016/0099046 A1 | 4/2016 | Liran | |
| 2016/0105968 A1 | 4/2016 | Tai et al. | |
| 2016/0220828 A1 | 8/2016 | Yan Poon et al. | |
| 2017/0368351 A1 | 12/2017 | Liran | |

FOREIGN PATENT DOCUMENTS

| | | |
|---|---|---|
| WO | 2011/086545 | 7/2011 |
| WO | 2012/017426 | 2/2012 |
| WO | 2012/114327 | 8/2012 |
| WO | 2012/153325 | 11/2012 |
| WO | 2014/080343 | 5/2014 |
| WO | 2014/141089 | 9/2014 |
| WO | 2015/101932 | 7/2015 |
| WO | 2015/110933 | 7/2015 |

OTHER PUBLICATIONS

Pham et al. Self Closing corneoscleral tunnel incision in cataract surgery, Opthalmaloge. Feb. 1996;93(1):8-1 1.

Yang et al. Surgical results of pars plana vitrectomy combined with phacoemulsification J Zhejian Univ Science B 20067(2):129-132.

An Office Action dated Feb. 23, 2018, which issued during the prosecution of U.S. Appl. No. 15/195,212.

An Invitation to pay additional fees dated Feb. 16, 2018, which issued during the prosecution of Applicant's PCT/IL2017/051202.

An Office Action dated Sep. 22, 2017, which issued during the prosecution of U.S. Appl. No. 15/195,212.

Roessler, G., Laube, T., Brockmann, C., Kirschkamp, T., Mazinani, B., Menzel-Severing, J., Bornfeld, N., Walter, P. and EPIRET Group, 2011. Angiographic findings following tack fixation of a wireless epiretinal retina implant device in blind RP patients. Graefe's Archive for Clinical and Experimental Ophthalmology, 249(9), pp. 1281-1286.

Ivastinovic, D., Langmann, G., Asslaber, M., Georgi, T., Wedrich, A. and Velikay-Parel, M., 2012. Distribution of glial fibrillary acidic protein accumulation after retinal tack insertion for intraocular fixation of epiretinal implants. Acta ophthalmologica, 90(5), pp. e416-e417.

Laube, T., Brockmann, C., Roessler, G., Walter, P., Krueger, C., Goertz, M., Klauke, S. and Bornfeld, N., 2012. Development of surgical techniques for implantation of a wireless intraocular epiretinal retina implant in Göttingen minipigs. Graefe's Archive for Clinical and Experimental Ophthalmology, 250(1), pp. 51-59.

Menzel-Severing, J., Sellhaus, B., Laube, T., Brockmann, C., Bornfeld, N., Walter, P. and Roessler, G., 2011. Surgical results and microscopic analysis of the tissue reaction following implantation and explantation of an intraocular implant for epiretinal stimulation in minipigs. Ophthalmic research, 46(4), pp. 192-198.

Gekeler, F., Szurman, P., Grisanti, S., Weiler, U., Claus, R., Greiner, T.O., Völker, M., Kohler, K., Zrenner, E. and Bartz-Schmidt, K.U., 2007. Compound subretinal prostheses with extra-ocular parts designed for human trials: successful long-term implantation in pigs. Graefe's Archive for Clinical and Experimental Ophthalmology, 245(2), pp. 230-241.

* cited by examiner

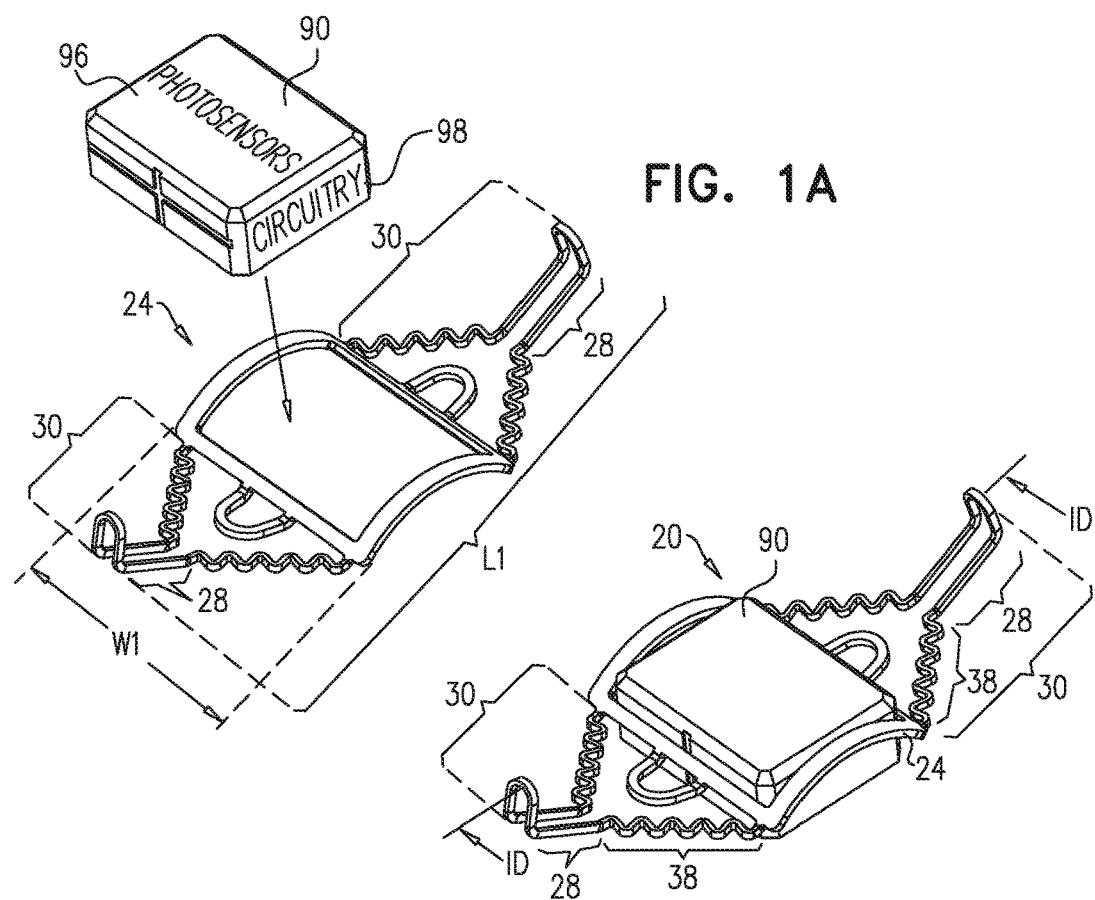
FIG. 1A
FIG. 1B
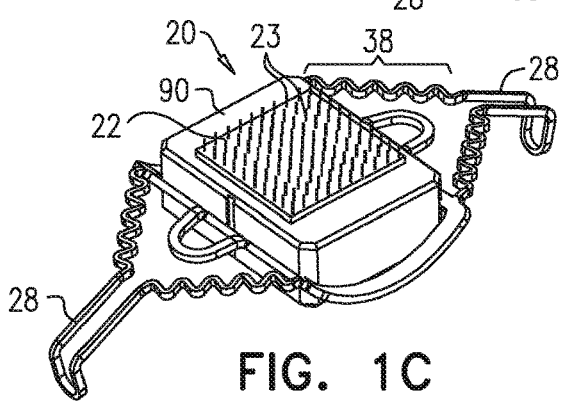
FIG. 1C
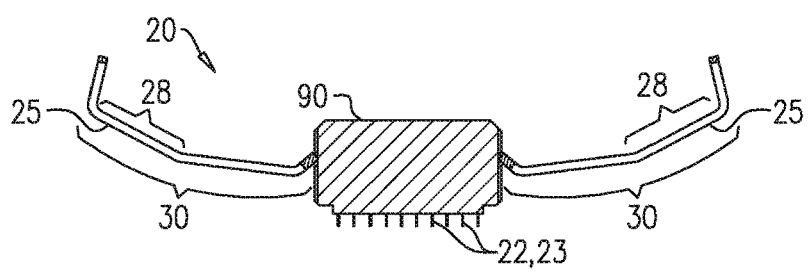
FIG. 1D

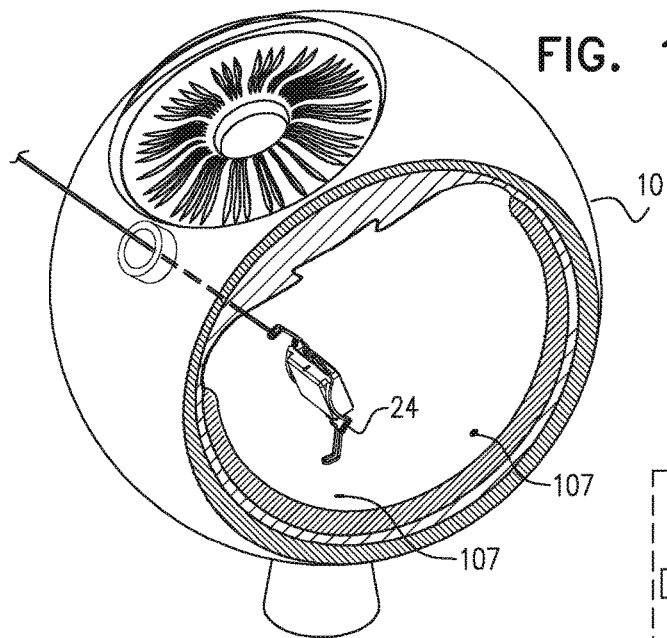
FIG. 1E
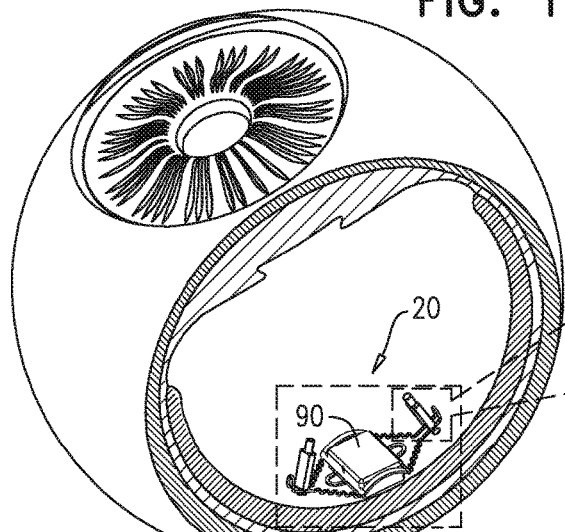
FIG. 1F
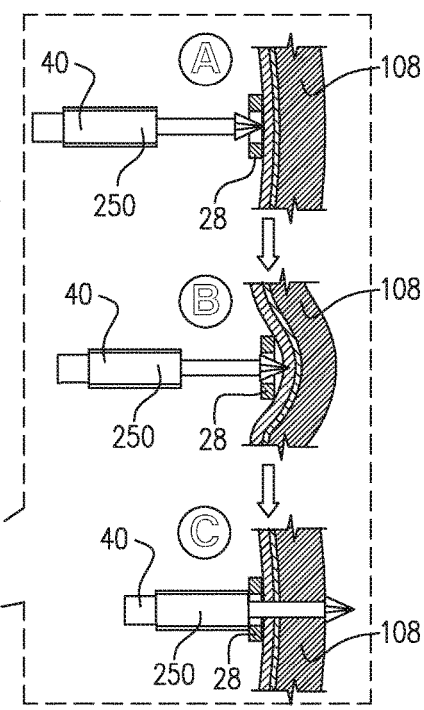
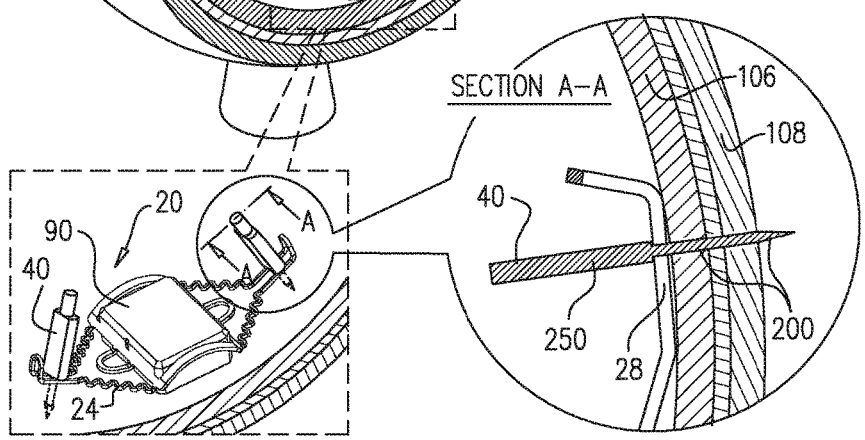
SECTION A-A

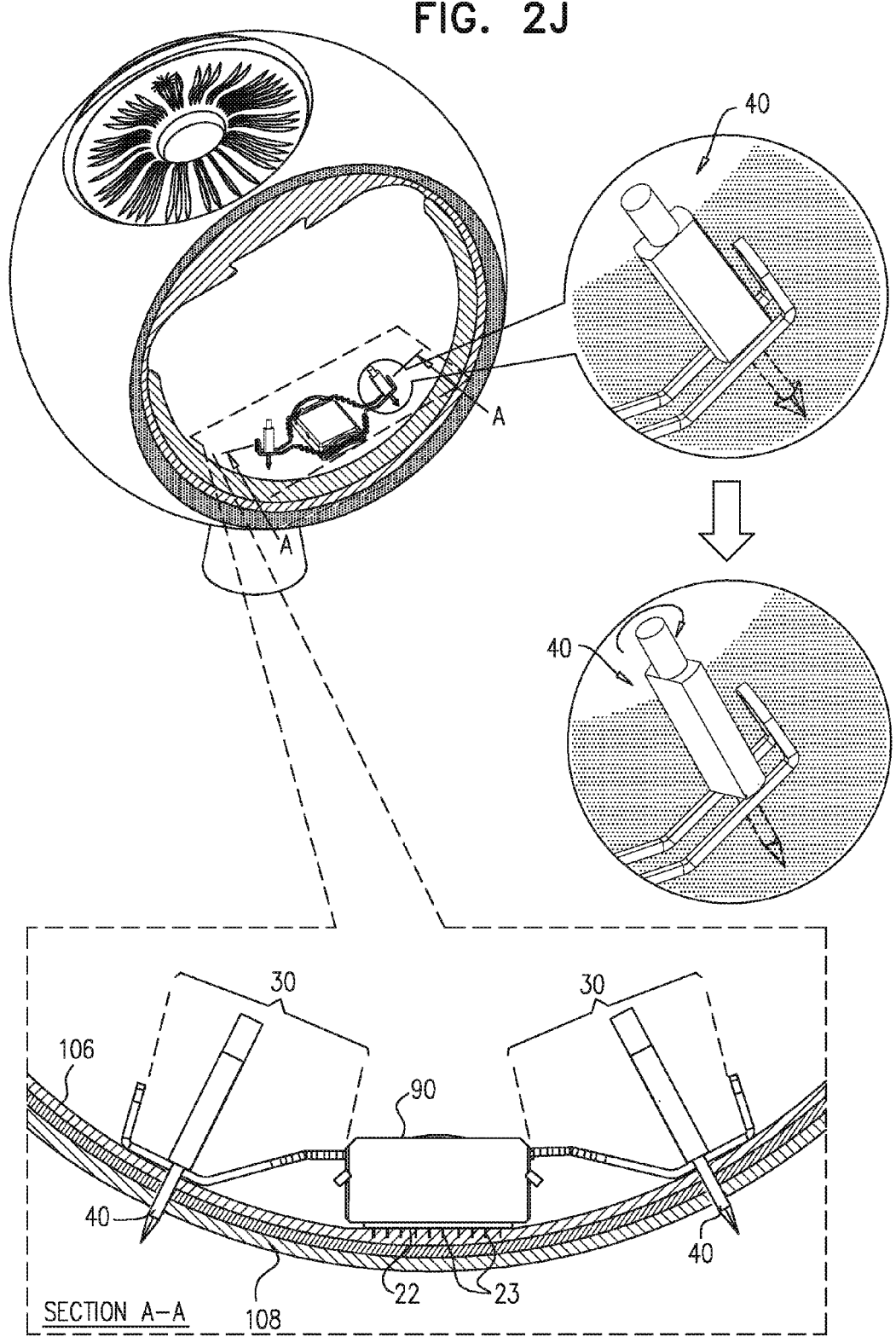

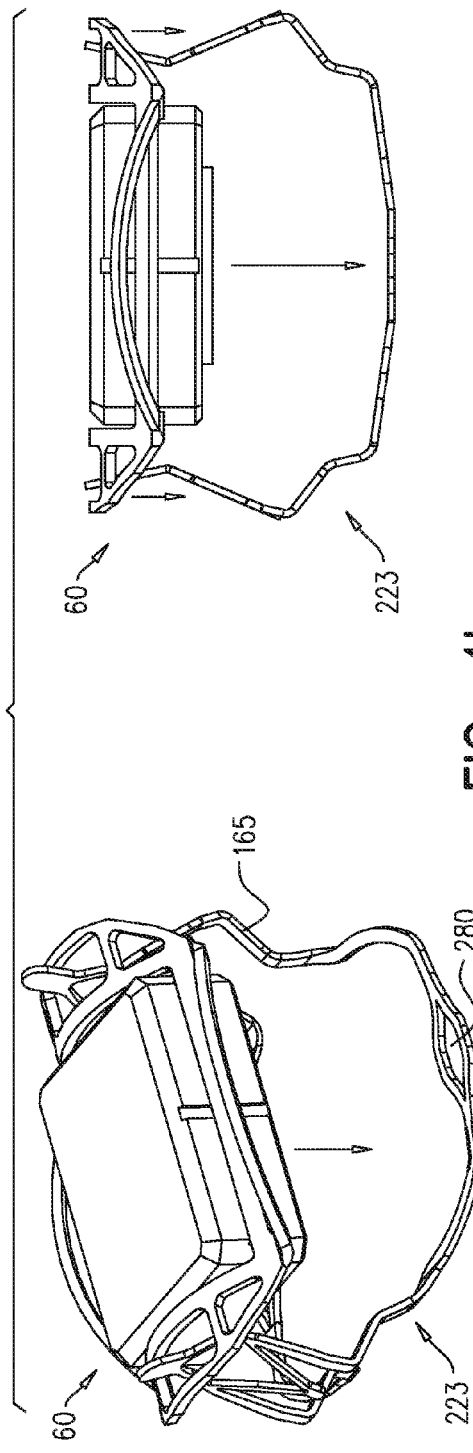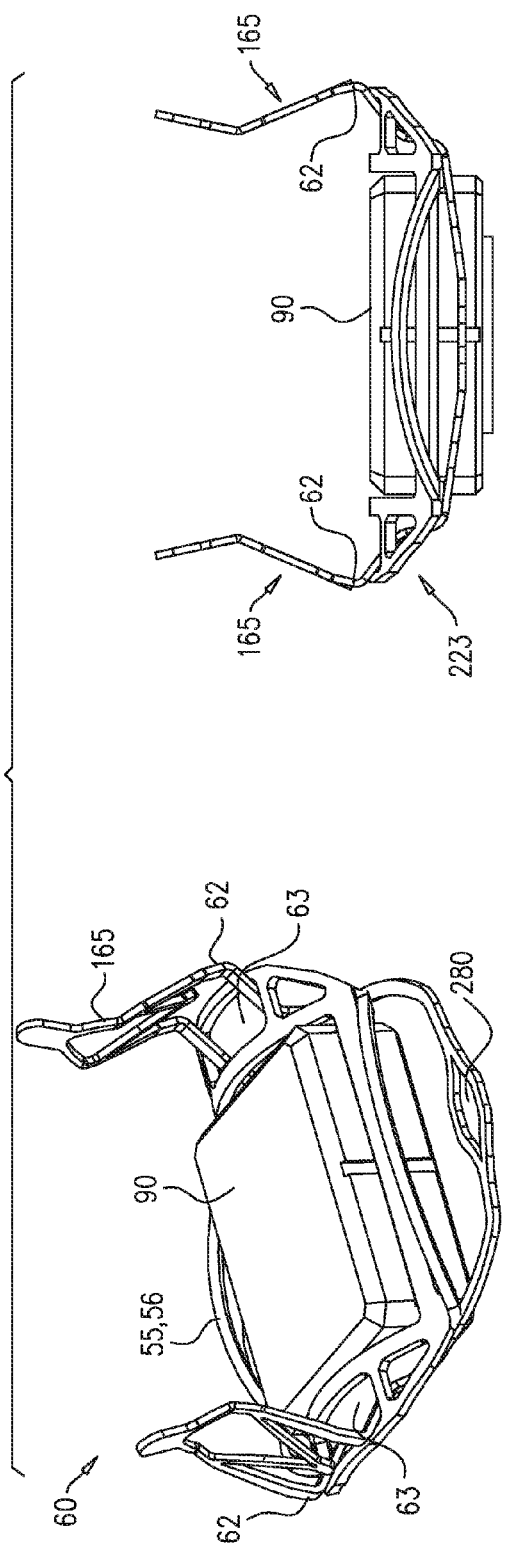

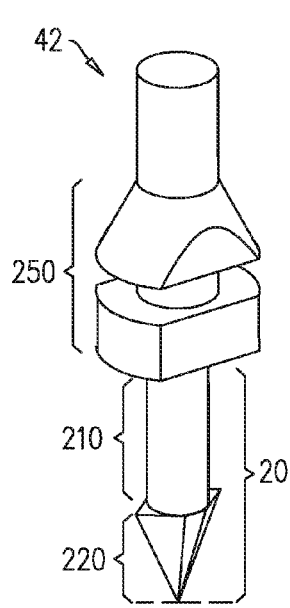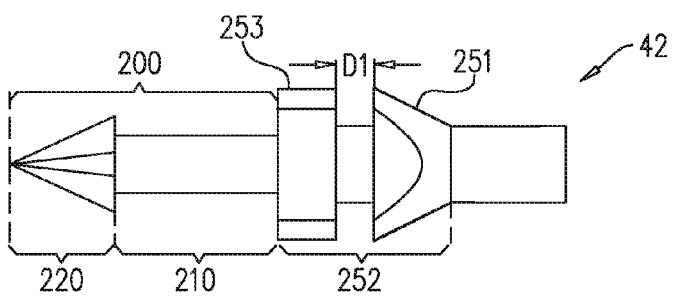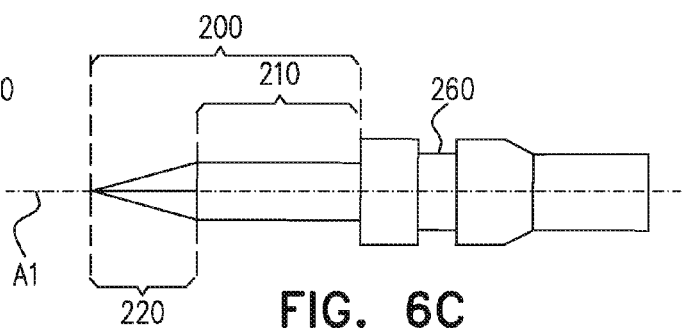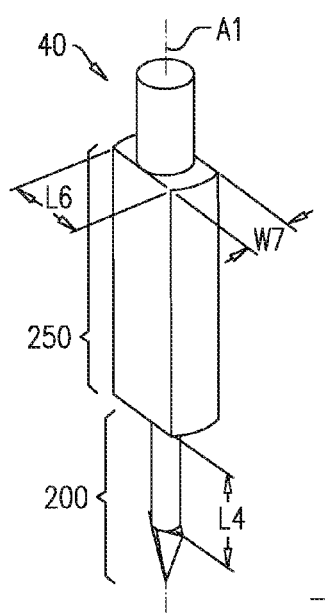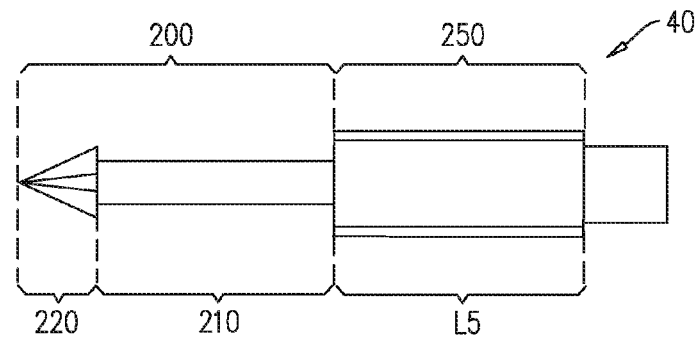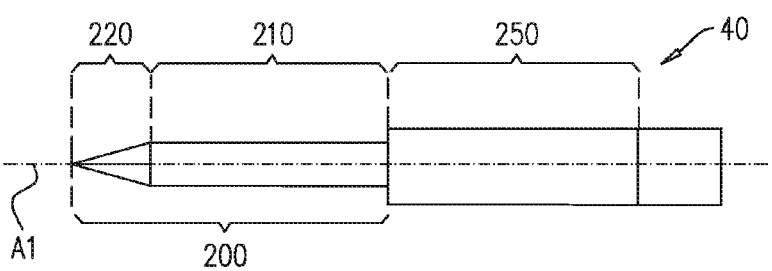

RETINAL IMPLANT FIXATION

CROSS-REFERENCE TO RELATED APPLICATIONS

The present application is related to U.S. application Ser. No. 15/342,765 to Weinberger et al., filed on Nov. 3, 2016, entitled, "Surgical Techniques for Implantation of a Retinal Implant," which is assigned to the assignee of the present application and is incorporated herein by reference.

FIELD OF THE INVENTION

The present invention relates generally to implantable medical devices, and specifically to a retinal prosthesis.

BACKGROUND

Retinal malfunction, due to degenerative retinal diseases, is a leading cause of blindness and visual impairment. Implantation of a retinal prosthesis is a technology for restoring some useful vision in individuals suffering from retina-related blindness.

The retina is a multi-layered light-sensitive structure that lines the posterior, inner part of the eye. The retina contains photoreceptor cells, for example rods and cones, which capture light and convert light signals into neural signals transmitted through the optic nerve to the brain. Rods are responsible for light sensitive, low resolution black and white vision, whereas cones are responsible for sharp, high resolution color vision. Most cones lie in the fovea, which defines the center of the retina, and which allows for maximum acuity of vision.

SUMMARY OF THE INVENTION

In some applications of the present invention, apparatus and methods are provided for securing an implantable retinal stimulator to an eye of a subject.

The implantable retinal stimulator is configured to stimulate a retina of the subject suffering from a retinal disease in order to restore at least partial vision in the subject. Typically, the implantable retinal stimulator comprises an electrode array comprising electrodes for stimulation of the retina, a plurality of photosensors, and driving circuitry configured to drive the electrodes to apply currents to the retina. The apparatus is typically implanted in an epi-retinal position, and the electrode array typically penetrates the retina. In accordance with some applications of the present invention, apparatus and methods for securing the implantable retinal stimulator to the retina are provided.

For example, a frame may be coupled to the implantable retinal stimulator and surround at least a portion of the implantable retinal stimulator. The frame is either an integral part of the implantable retinal stimulator or a separate frame which is coupled to the implantable retinal stimulator. The frame is typically shaped to define at least a first anchoring element receiving portion. An anchoring element is positioned in the anchoring element receiving portion of the frame and penetrates the sclera of the subject's eye to secure the implantable retinal stimulator to the retina. Other applications for securing and anchoring the implantable retinal stimulator are also described.

There is therefore provided in accordance with some applications of the present invention, apparatus, including:

an implantable retinal stimulator, configured for implantation on a retina of a subject's eye, and including (i) an electrode array including electrodes; (ii) a plurality of photosensors; and (iii) driving circuitry, configured to drive the electrodes to apply currents to the retina;

an interface member disposed at an outer surface of the implantable retinal stimulator;

a frame, (i) shaped and sized to couple to the interface member and to surround the implantable retinal stimulator at least in part, and (ii) shaped to define at least a first anchoring element receiving portion; and an anchoring element shaped and sized to be positioned in the anchoring element receiving portion and to penetrate scleral tissue of the subject.

For some applications, the interface member includes a peripheral member surrounding at least a portion of the implantable retinal stimulator.

For some applications, the peripheral member is shaped as a rim of the implantable retinal stimulator.

For some applications, the rim includes at least one connecting protruding element shaped and sized to press against the frame to maintain the frame coupled to the rim.

For some applications, the frame is shaped to define at least a first extension portion, the first extension portion shaped to define the at least one anchoring element receiving portion.

For some applications, the frame is shaped to define a second extension portion, opposite the first extension portion, and shaped to define a second anchoring element receiving portion.

For some applications, the first and second extension portions are each geometrically shaped to increase flexibility of the first and second extension portions versus if the first and second extension portions were straight.

For some applications, the first and second extension portions are each shaped at least in part as a shape selected from the group consisting of: a repeating wave pattern and an undulating pattern.

For some applications, the first and second anchoring element receiving portions each include a tissue-contact surface configured to contact a surface of the retina when the apparatus is implanted on the retina.

For some applications, the first anchoring element receiving portion is not parallel to the second anchoring element receiving portion when the first and second anchoring element receiving portions are unconstrained.

For some applications, the first and second anchoring element receiving portions are each not parallel to the electrode array when the first and second anchoring element receiving portions are unconstrained.

For some applications, the frame is shaped to define first and second guiding surfaces extending away from the first and second anchoring element receiving portions, and configured to guide the implantable retinal stimulator into the frame.

For some applications, the interface member is shaped to define a first and a second window, and the first and second guiding surfaces are configured to guide the implantable retinal stimulator into the frame by the first and second guiding surfaces being inserted into the first and second windows.

For some applications, the apparatus further includes an implantation needle, and the frame is shaped and sized to be deployed through the implantation needle.

There is further provided in accordance with some applications of the present invention, a method for implanting, in an eye of a subject, apparatus including (a) an implantable retinal stimulator configured for implantation on a retina of the subject's eye, having (i) an electrode array including electrodes; (ii) a plurality of photosensors; and (iii) driving circuitry, configured to drive the electrodes to apply currents to the retina, and (b) an interface member disposed at an outer surface of the implantable retinal stimulator, the method including:

positioning the apparatus in an epi-retinal position such that the electrode array penetrates the retina; and advancing an anchoring element into an anchoring element receiving portion of a frame surrounding the implantable retinal stimulator at least in part, such that the anchoring element penetrates scleral tissue of the subject.

For some applications the method further includes, prior to the advancing, securing the frame to the interface member such that the frame surrounds the implantable retinal stimulator at least in part.

For some applications the method further includes, prior to the advancing and subsequently to the positioning, securing the frame to the interface member such that the frame surrounds the implantable retinal stimulator at least in part.

For some applications, the frame is an integral part of the apparatus, and positioning includes positioning the implantable retinal stimulator surrounded at least in part by the frame.

For some applications the method further includes, prior to positioning the apparatus, marking on the retina a location for advancing the anchoring element into the scleral tissue of the subject, and advancing the anchoring element includes advancing the anchoring element into the marked location.

For some applications, marking the location includes applying light to the retina at the location.

For some applications, applying the light includes denaturing protein of the retina by applying laser light.

For some applications, applying the light includes applying the light prior to and while advancing the anchoring element, and advancing the anchoring element includes advancing the anchoring element into the marked location.

For some applications the method further includes, rotating the anchoring element subsequently to the anchoring element penetrating the scleral tissue.

For some applications, the anchoring element has a longitudinal axis in the direction of the advancing, and the anchoring element is shaped to define a non-circular cross-section in a plane transverse to the longitudinal axis.

There is further provided in accordance with some applications of the present invention, apparatus, including:

an implantable retinal stimulator, configured for implantation on a retina of a subject's eye, and including (i) an electrode array including electrodes; (ii) a plurality of photosensors; and (iii) driving circuitry, configured to drive the electrodes to apply currents to the retina;

a frame, (i) shaped and sized to couple to the implantable retinal stimulator and to surround the implantable retinal stimulator at least in part, and (ii) shaped to define at least one anchoring element receiving portion; and an anchoring element shaped and sized to be positioned in the at least one anchoring element receiving portion and to penetrate scleral tissue of the subject.

For some applications, the frame has a length of 6-15 mm.
For some applications, the frame has a width of 4-10 mm.
For some applications, the frame is shaped to define at least a first extension portion, the first extension portion shaped to define the at least one anchoring element receiving portion.

For some applications, the frame is shaped to define a second extension portion, opposite the first extension portion, and shaped to define a second anchoring element receiving portion.

For some applications, the frame is (a) shaped to define first and second guiding surfaces extending away from the first and second anchoring element receiving portions, and (b) configured to guide the implantable retinal stimulator into the frame.

For some applications, the first and second extension portions are each geometrically shaped to increase flexibility of the first and second extension portions versus if the first and second extension portions were straight.

For some applications, the first and second extension portions are each shaped at least in part as a shape selected from the group consisting of: a repeating wave pattern and an undulating pattern.

For some applications, the first and second anchoring element receiving portions each include a tissue-contact surface configured to contact a surface of the retina when the apparatus is implanted on the retina.

For some applications, the first anchoring element receiving portion is not parallel to the second anchoring element receiving portion when the first and second anchoring element receiving portions are unconstrained.

For some applications, the first and second anchoring element receiving portions are each not parallel to the electrode array when the first and second anchoring element receiving portions are unconstrained.

For some applications, the anchoring element includes:
a tissue penetrating portion, including (i) a cylindrical shaft 0.4-1.2 mm in length, and (ii) a puncturing tip and disposed distal to the cylindrical shaft; and a proximal portion, 1.5-3 mm in length, extending along a longitudinal axis of the anchoring element, proximal to the tissue penetrating portion, and having:
   (i) a cross-sectional area, in a plane perpendicular to the longitudinal axis of the anchoring element, that is greater than a cross-sectional area of the cylindrical shaft, in a plane perpendicular to the longitudinal axis of the anchoring element, and
   (ii) a non-circular cross-sectional shape in a plane transverse to the longitudinal axis.

There is further provided in accordance with some applications of the present invention, apparatus, including a longitudinal anchoring element including:
a tissue penetrating portion, including (i) a cylindrical shaft 0.4-1.2 mm in length, and (ii) a puncturing tip disposed distal to the cylindrical shaft; and a proximal portion, 1-3 mm in length, extending along a longitudinal axis of the anchoring element, proximal to the tissue penetrating portion, and having:
   (i) a cross-sectional area, in a plane perpendicular to the longitudinal axis of the anchoring element, that is greater than a cross-sectional area of the cylindrical shaft, in a plane perpendicular to the longitudinal axis of the anchoring element, and
   (ii) a non-circular cross-sectional shape in a plane transverse to the longitudinal axis.

For some applications, the cylindrical shaft has a circular-cross section.

There is further provided in accordance with some applications of the present invention, apparatus, including:

an implantable retinal stimulator, configured for implantation on a retina of a subject's eye, and including (i) an electrode array including electrodes; (ii) a plurality of photosensors; and (iii) driving circuitry, configured to drive the electrodes to apply currents to the retina; and an elastic anchoring element coupled to the implantable retinal stimulator, a length of the anchoring element when unconstrained being 1.3-2 cm.

For some applications, the elastic anchoring element is shaped to define an elastic conical helical element coupled to the implantable retinal stimulator at a vertex of the conical helical anchoring element.

For some applications, the elastic anchoring element is shaped to define a proximal end and a distal end, the distal end being at the vertex of the elastic anchoring element, and coupled to the implantable retinal stimulator such that the proximal end applies a force to an area that is within 4 mm of an ora serrata of the eye when the implantable retinal stimulator is implanted on the retina of the subject's eye.

There is further provided in accordance with some applications of the present invention, a method for implanting apparatus in an eye of a subject, the method including:

providing apparatus including (a) an implantable retinal stimulator, configured for implantation on a retina of a subject's eye, and having (i) an electrode array including electrodes; (ii) a plurality of photosensors; and (iii) driving circuitry, configured to drive the electrodes to apply currents to the retina, and (b) an elastic anchoring element coupled to the implantable retinal stimulator; and positioning the apparatus, in an epi-retinal position such that (i) the electrode array penetrates the retina; (ii) a distal end of the elastic anchoring element is coupled to the implantable retinal stimulator and does not penetrate tissue of the subject; and (iii) a proximal end of the elastic anchoring element applies a force to an area that is within 4 mm of an ora serrata of the eye.

For some applications, positioning the apparatus does not include a step of penetrating scleral tissue of the eye with a tack.

For some applications, positioning the apparatus does not include a step of penetrating scleral tissue of the eye.

There is further provided in accordance with some applications of the present invention, a method for implanting, in an eye of a subject, apparatus including (a) an implantable retinal stimulator, configured for implantation on a retina of a subject's eye, and having (i) an electrode array including electrodes; (ii) a plurality of photosensors; and (iii) driving circuitry, configured to drive the electrodes to apply currents to the retina, and (b) a frame surrounding at least a portion of the implantable retinal stimulator, the method including:

penetrating scleral tissue of the subject by advancing at least one anchoring element into the scleral tissue; and subsequently, positioning the apparatus in an epi-retinal position such that (i) the electrode array penetrates the retina, and (ii) the frame is engaged with the at least one anchoring element such that the apparatus is secured to the retina.

For some applications the method further includes, prior to penetrating, marking on the retina a location for advancing the anchoring element into the scleral tissue of the subject, and advancing the anchoring element includes advancing the anchoring element into the marked location.

For some applications, marking the location includes:
placing a guide template against the retina; and
marking the location using the guide template.

For some applications, marking the location using the guide template includes marking the location based on a shape of the guide template.

For some applications the method further includes, subsequently to the marking, removing the guide template.

For some applications, marking the location includes applying light to the retina at the location.

For some applications, applying the light includes denaturing protein of the retina by applying laser light.

For some applications, applying the light includes applying the light prior to and while advancing the anchoring element, and advancing the anchoring element includes advancing the anchoring element into the marked location.

There is further provided in accordance with some applications of the present invention, a method for implanting, in an eye of a subject, apparatus including (a) an implantable retinal stimulator, configured for implantation on a retina of a subject's eye, and having (i) an electrode array including electrodes; (ii) a plurality of photosensors; and (iii) driving circuitry, configured to drive the electrodes to apply currents to the retina, and (b) a frame for surrounding at least a portion of the implantable retinal stimulator and being shaped to define at least one anchoring element receiving portion, the method including:

positioning the frame in an epi-retinal position on a retina of the subject;

subsequently, positioning the implantable retinal stimulator in the frame such that (i) the frame surrounds at least a portion of the implantable retinal stimulator, and (ii) the electrode array penetrates the retina; and advancing an anchoring element into the at least one anchoring element receiving portion such that the anchoring element penetrates scleral tissue of the subject.

For some applications, advancing the anchoring element includes advancing the anchoring element subsequently to the positioning of the implantable retinal stimulator in the frame.

For some applications, advancing the anchoring element into the at least one anchoring element receiving portion includes advancing the anchoring element prior to the positioning of the implantable retinal stimulator in the frame.

For some applications, advancing the anchoring element includes advancing the anchoring element into the scleral tissue prior to the positioning of the frame.

For some applications, positioning the implantable retinal stimulator in the frame includes snapping the implantable retinal stimulator to the frame.

The present invention will be more fully understood from the following detailed description of applications thereof, taken together with the drawings, in which:

BRIEF DESCRIPTION OF THE DRAWINGS

FIGS. 1A-F are schematic illustrations of apparatus for implantation in an eye of a subject, in accordance with some applications of the present invention;

FIGS. 2A-J are schematic illustrations of apparatus for implantation in an eye of a subject, in accordance with some applications of the present invention;

FIGS. 4A-I are schematic illustrations of apparatus for implantation in an eye of a subject, in accordance with some applications of the present invention;

FIGS. 6A-C are schematic illustrations of an anchoring element, in accordance with some applications of the present invention;

FIGS. 7A-C are schematic illustrations of an anchoring element, in accordance with some applications of the present invention.

DETAILED DESCRIPTION OF EMBODIMENTS

Figure 2A:
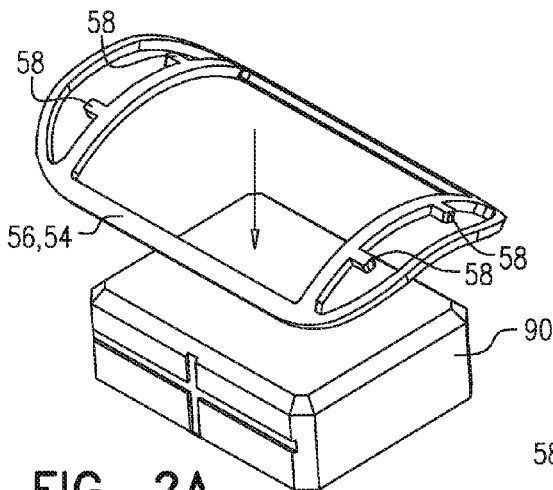
Figure 2B:
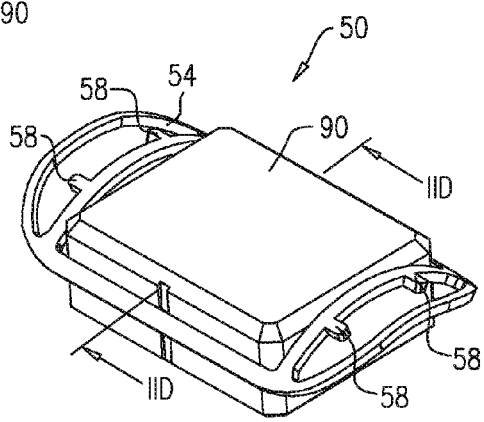
Figure 2C:
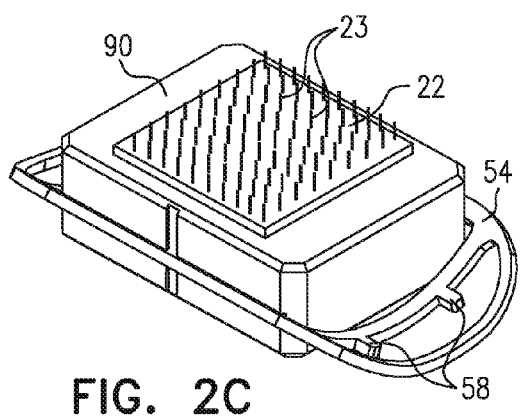
Figure 2D:
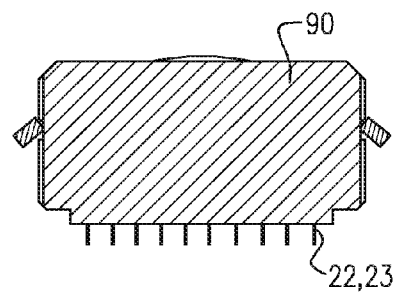
Figure 2E:
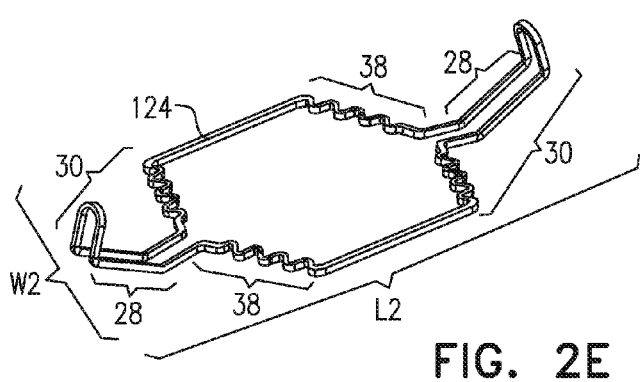

Some applications of the present invention provide apparatus and methods for securing an implantable retinal stimulator 90 to an eye of a subject. The following detailed description provides examples for such apparatus and methods for securing implantable retinal stimulator 90 in accordance with applications of the present invention.

Reference is first made to FIGS. 1A-F, which are schematic illustrations of apparatus 20 for implantation in an eye of a subject, in accordance with some applications of the present invention. Apparatus 20 typically comprises implantable retinal stimulator 90 configured for implantation on a retina of a subject's eye, and frame 24 which is shaped and sized to couple to implantable retinal stimulator 90 and to surround implantable retinal stimulator 90 at least in part. Typically, frame 24 is used to fix implantable retinal stimulator 90 to the retina by means of anchoring elements that engage frame 24. Typically, having a frame 24 that is separate from implantable retinal stimulator 90 allows movement of implantable retinal stimulator 90 and frame 24 with respect to each other, thereby absorbing forces.

Implantable retinal stimulator 90 typically comprises an electrode array 22 comprising a plurality of electrodes 23 configured to penetrate the retina of the subject when implantable retinal stimulator 90 is positioned on the retina. It is noted that the scope of the present invention includes electrode array 22 having electrodes that do not penetrate the retina, e.g., surface electrodes. Array 22 typically comprises 400-3000 electrodes.

Typically, implantable retinal stimulator 90 additionally comprises a plurality of photosensors 96, each photosensor configured to detect photons and generate a signal in response thereto, and driving circuitry 98, configured to receive the signal from the photosensors and to drive the electrodes to apply currents to the retina to stimulate the retina.

Frame 24, which surrounds implantable retinal stimulator 90 at least in part, is typically shaped to define at least one anchoring element receiving portion 28 which is configured to receive an anchoring element for securing implantable retinal stimulator 90 and frame 24 to the retina. As shown in FIGS. 1A-F, frame 24 is shaped to define two, i.e., a first and a second, anchoring element receiving portions 28, although for some applications a single anchoring element receiving portion 28 is used, or more than two anchoring element receiving portion 28 is used.

Typically, frame 24 has a length L1 that is at least 6 mm and/or less than 15 mm. Frame 24 typically has a width W1 of at least 4 mm and/or less than 10 mm.

For some applications, frame 24 is shaped to define at least a first extension portion 30. Typically, frame 24 is shaped to define two, i.e., first and second extension portions 30, as shown. When implantable retinal stimulator 90 is surrounded by frame 24, first and second extension portions 30 extend away from implantable retinal stimulator 90. Each extension portion 30 is shaped to define anchoring element receiving portion 28. As additionally shown in FIGS. 1A-F, first and second extension portions 30 are each geometrically shaped, at least in part, to increase flexibility of first and second extension portions 30 versus if first and second extension portions 30 were straight. For example, portions 38 of first and second extension portions 30 are each shaped as a shape selected from, the group consisting of: a repeating wave pattern and an undulating pattern (e.g., sinusoid, square, and/or a wave).

For some applications, frame 24 is shaped such, that first and second anchoring element receiving portions 28 are not parallel to each other when unconstrained. Additionally, for these applications, anchoring element receiving portions 28 are each not parallel to electrode array 22 when anchoring element receiving portions 28 are unconstrained. This use of non-parallel components, as shown in the figures and described, facilitates implantable retinal stimulator 90 and frame 24 conforming to the curved surface of the retina.

Anchoring element receiving portions 28 each comprise a tissue-contact surface 25 configured to contact a surface of the retina when apparatus 20 is implanted on the retina.

In accordance with some applications of the present invention, apparatus 20 further comprises at least one anchoring element 40, e.g., a tack, shaped and sized to be positioned in anchoring element receiving portion 28 and to penetrate scleral tissue 108 of the subject.

Reference is made to FIGS. 1E-F which show implantation of apparatus 20 in eye 10 of the subject. Typically, prior to implantation in eye 10, frame 24 is secured to implantable retinal stimulator 90 (this can be done during manufacture of stimulator 90 and frame 24, or alternatively, frame 24 can be secured to stimulator 90 by the physician). Frame 24 and implantable retinal stimulator 90 are then positioned in the eye, typically, in an epi-retinal position such that electrode array 22 penetrates retina 106. (For some applications, frame 24 and implantable retinal stimulator 90 are placed after marking one or more locations 107 on the retina, using techniques described hereinbelow.)

Anchoring element 40 is advanced into anchoring element receiving portion 28 such that the anchoring element penetrates scleral tissue 108 of the subject. As shown, for some applications, at least one anchoring element 40 is advanced into each anchoring element receiving portion 28. Typically, anchoring element 40 is rotated subsequently to penetrating scleral tissue 108. Rotating anchoring element 40 typically locks element 40 into frame 24 thereby facilitating securing of apparatus 20 to eye 10. FIG. 1F shows element 40 after being rotated into the locked position.

Alternatively, prior to positioning apparatus 20 on the retina, one or more locations 107 on the retina are marked, and anchoring elements 40 are advanced into the marked locations. Subsequently, frame 24 and implantable retinal stimulator 90 are positioned on the retina such that electrode array 22 penetrates retina 106 and frame 24 engages anchoring element 40, e.g., by sliding over the anchoring element. Typically, anchoring element 40 is then rotated to lock element 40 in place. For some applications, marking the location 107 on the retina comprises puncturing the retina at the location. Alternatively, marking the location on the retina is performed by applying light to the retina at the location. For example, laser light may be applied to location 107 causing denaturing of protein and marking the location by burning the tissue at the location. For some applications the light is applied to mark the location on the retina prior to, and while, the anchoring element is advanced, e.g., using a laser (not shown).

Reference is now made to FIGS. 2A-J which are schematic illustrations of apparatus 50 for implantation in an eye of a subject, in accordance with some applications of the present invention. Typically, apparatus 50 comprises implantable retinal stimulator 90 for stimulation of the retina. Apparatus 50 further comprises an interface member 56 disposed at an outer surface of the implantable retinal stimulator. For example, interface member 56 may comprise a peripheral member such as a rim 54, which surrounds at least a portion of implantable retinal stimulator 90 (rim 54 being either an integral part of implantable retinal stimulator 90 or a separate rim which is coupled to implantable retinal stimulator 90). Another component of apparatus 50 is a frame 124 (shown in FIG. 2E). Frame 124 typically has a length L2 of 10-15 mm, e.g., 12 mm and width W2 of 5-10 mm, e.g., 7 mm. Frame 124 is shaped to define at least a first anchoring element receiving portion 28. Typically, as shown, frame 124 is shaped to define two (first and second) anchoring element receiving portions 28.

For some applications, frame 124 is shaped to define at least a first extension portion 30. Typically, frame 124 is shaped to define first and second extension portions 30, as shown. When implantable retinal stimulator 90 is surrounded by frame 24, first and second extension portions 30 extend away from implantable retinal stimulator 90. Each extension portion 30 is shaped to define anchoring element receiving portion 28. As further shown in FIGS. 2A-J, first and second extension portions 30 are each geometrically shaped, at least in part, to increase flexibility of first and second extension portions 30 versus if first and second extension portions 30 were straight. For example, portions 38 of first and second extension portions 30 are each shaped at least in part as a shape selected from the group consisting of: a repeating wave pattern and an undulating pattern (e.g., sinusoid, square, and/or a wave).

Frame 124 is shaped such that first and second anchoring element receiving portions 28 are not parallel to each other when unconstrained. Additionally, anchoring element receiving portions 28 are each not parallel to electrode array 22 when anchoring element receiving portions 28 are unconstrained.

Anchoring element receiving portions 28 each comprise a tissue-contact surface 25 configured to contact a surface of the retina when apparatus 20 is implanted on the retina.

In accordance with some applications of the present invention, apparatus 50 further comprises at least one anchoring element 40, e.g., a tack, shaped and sized to be positioned in anchoring element receiving portion 28 and to penetrate scleral tissue 108 of the subject. Anchoring element 40 secures apparatus 50 to the eye by penetrating tissue of the eye (e.g., sclera tissue).

Figure 2F:
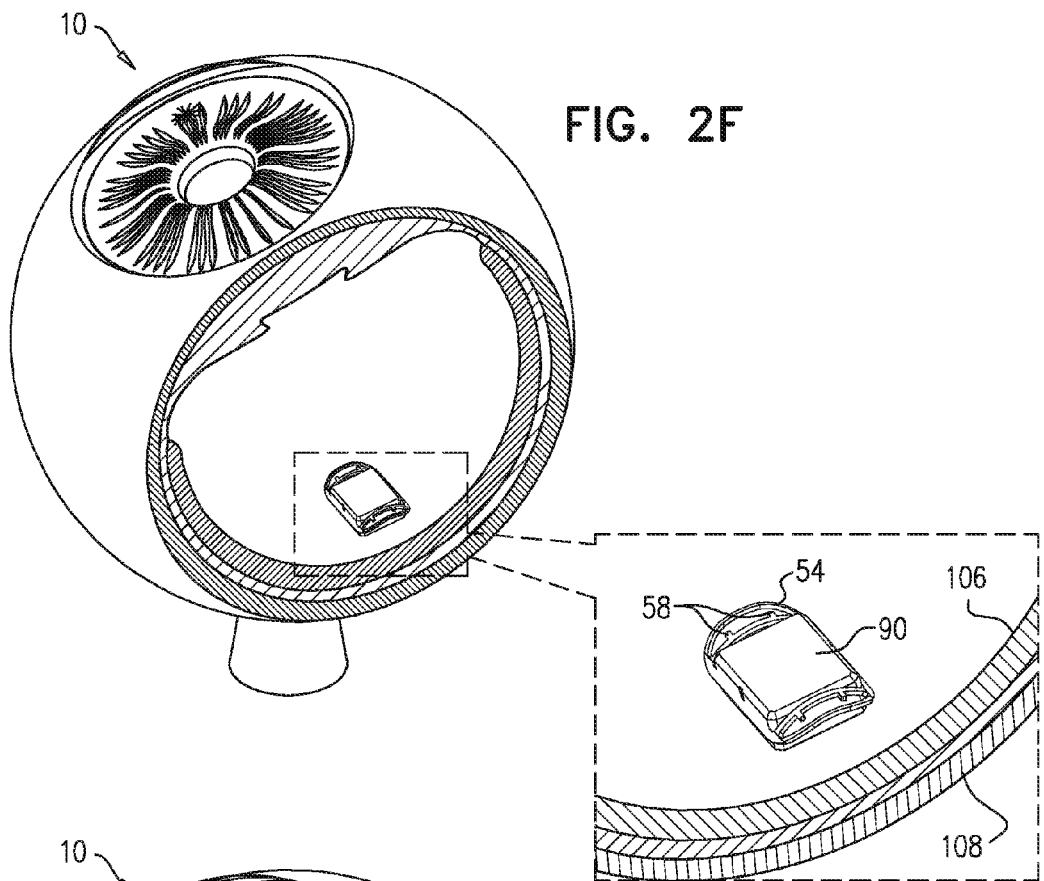
Figure 2G:
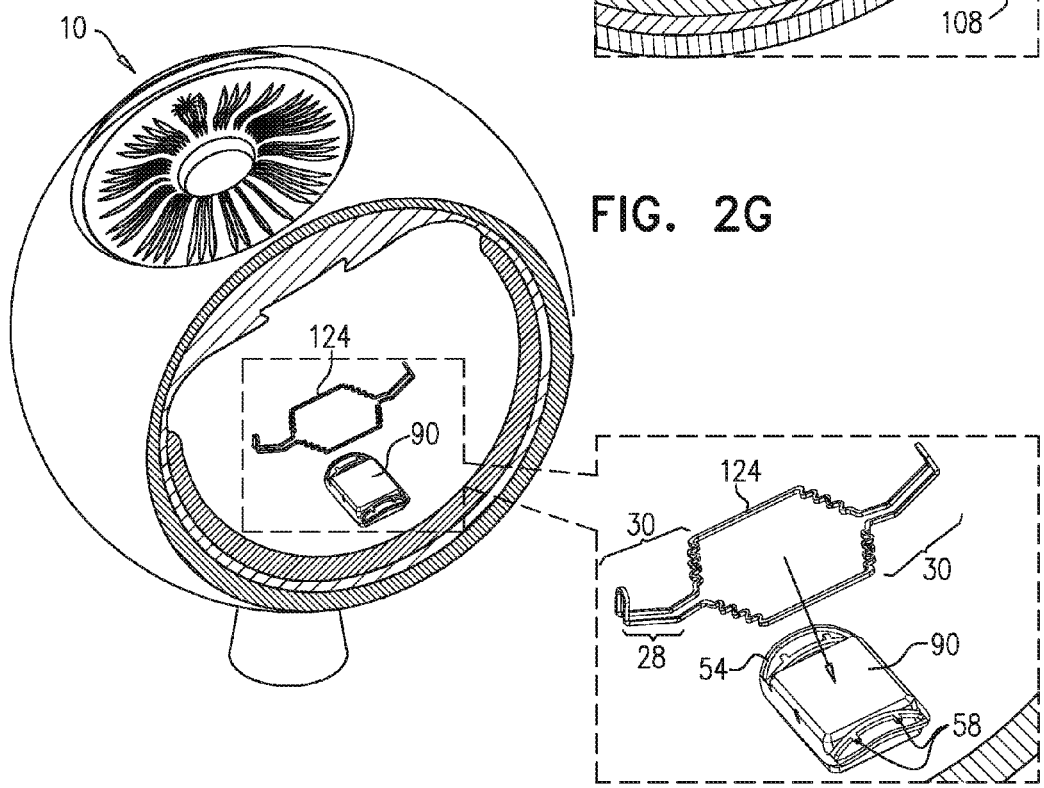
Figure 2H:
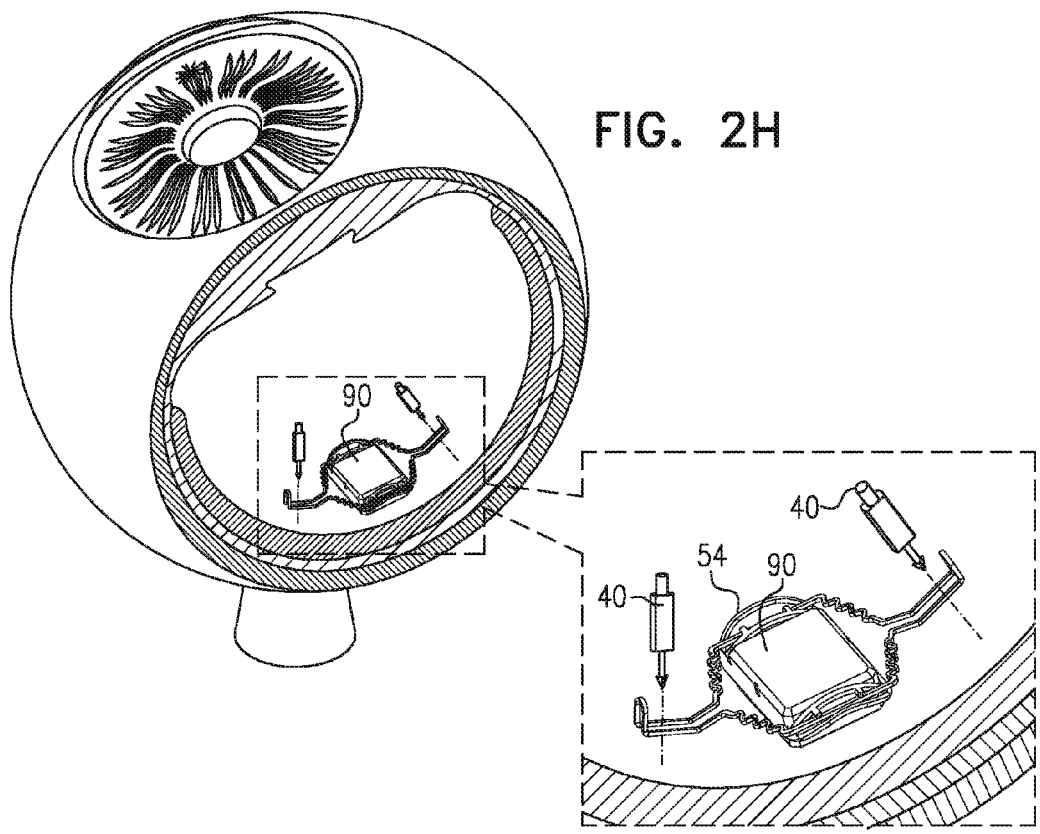

Reference is made to FIGS. 2F-J, which are schematic illustrations of implantation of apparatus 50 in eye 10 of the subject. Typically, prior to implantation in eye 10, rim 54 is secured to implantable retinal stimulator 90 (shown in FIGS. 2A-C). Securing rim 54 to implantable retinal stimulator 90 can be done during manufacture of implantable retinal stimulator 90 and rim 54, or alternatively, rim 54 can be secured to implantable retinal stimulator 90 by the physician prior to implantation. Implantable retinal stimulator 90, surrounded at least in part by rim 54, is then positioned in eye 10 typically in an epi-retinal position such that electrode array 22 penetrates retina 106 (FIG. 2F). Frame 124 is then advanced toward the retina (FIG. 2G) and secured to rim 54 such that frame 124 surrounds electrode array 22 at least in part. Frame 124 is typically secured to rim 54 by pressing against at least one, e.g., four, connecting protruding elements 58 of rim 54 (which may, for example, be shaped like teeth) (FIG. 2H). Typically, having frame 124 and stimulator 90 as separate components allows for motion of the frame with respect to stimulator 90. Alternatively, for other applications, frame 124 is an integral part of stimulator 90. For some applications, apparatus 50 further comprises an implantation needle and frame 124 is deployed in eye through the implantation needle (not shown).

Figure 2I:
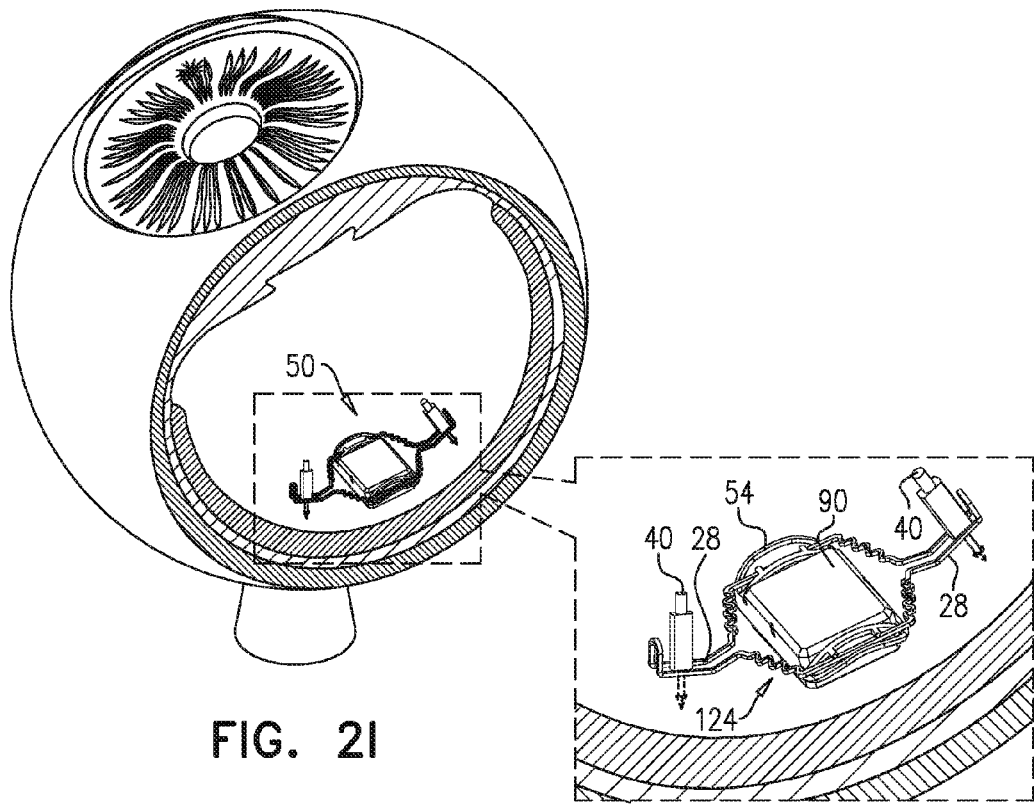

Typically, anchoring element 40 is advanced into anchoring element receiving portion 28 such that the anchoring element penetrates scleral tissue 108 of the subject (FIGS. 2H-J). As shown, for some applications, at least one anchoring element 40 is advanced into each anchoring element receiving portion 28. Typically, anchoring element 40 is rotated subsequently to penetrating scleral tissue (FIG. 2J). Rotating anchoring element 40 typically locks element 40 into frame 124 thereby facilitating securing of apparatus 50 to eye 10.

For some applications, prior to positioning apparatus 50 on the retina, a location on the retina is marked and anchoring element 40 is advanced into the marked location. Subsequently, frame 124 is positioned on the retina such that frame 124 engages anchoring element 40. Typically, anchoring element 40 is then rotated to lock element 40 in place. Implantable retinal stimulator 90 surrounded by rim 54 is then positioned in frame 124 and secured to frame 124.

For some applications, marking the location on the retina comprises puncturing the retina at the location. Alternatively, marking the location on the retina is done by applying light, to the retina at the location. For example, laser light is applied to the location causing thereby denaturing of protein and marking the location by burning the tissue at the location. For some applications the light is applied to mark the location on the retina prior to, and while, the anchoring element is advanced.

Figure 3A:
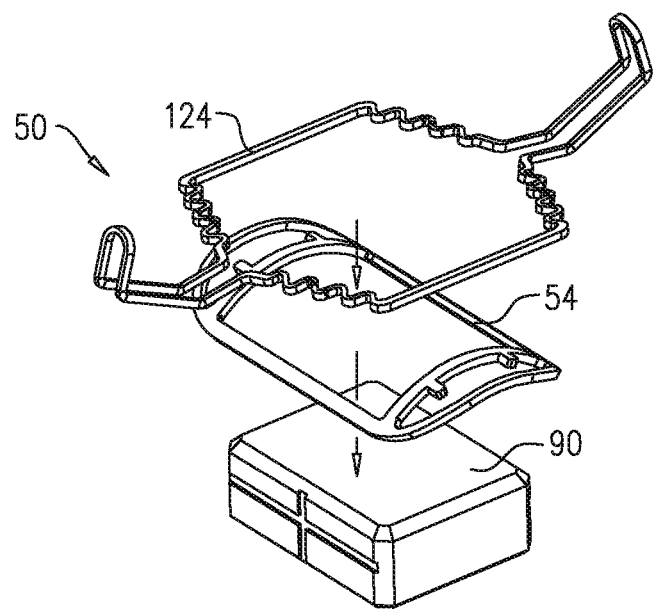
FIGS. 3A-B are schematic illustrations of apparatus for implantation in an eye of a subject, in accordance with some applications of the present invention.
Figure 3B:
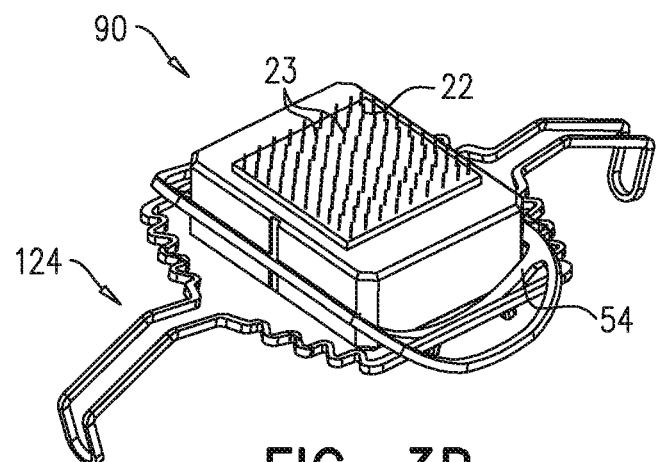

Reference is now made to FIGS. 3A-B. For some applications, frame 124 is secured to implantable retinal stimulator 90 by means of rim 54 prior to implantation in eye 10 of the subject. Securing frame 124 to rim 54 can be done during manufacture, or alternatively, frame 124 can be secured to implantable retinal stimulator 90 by the physician directly prior to implantation. For such applications, an assembly of frame 124 secured to rim 54, which in turn surrounds implantable retinal stimulator 90, is advanced into eye 10 and positioned in an epi-retinal position such that array 22 penetrates retina 106. As described hereinabove, with reference to FIG. 1E and FIGS. 2H-J, at least one anchoring element 40 or 42 is advanced into frame 124 to secure implantable apparatus 50 to the eye.

Figure 4A:
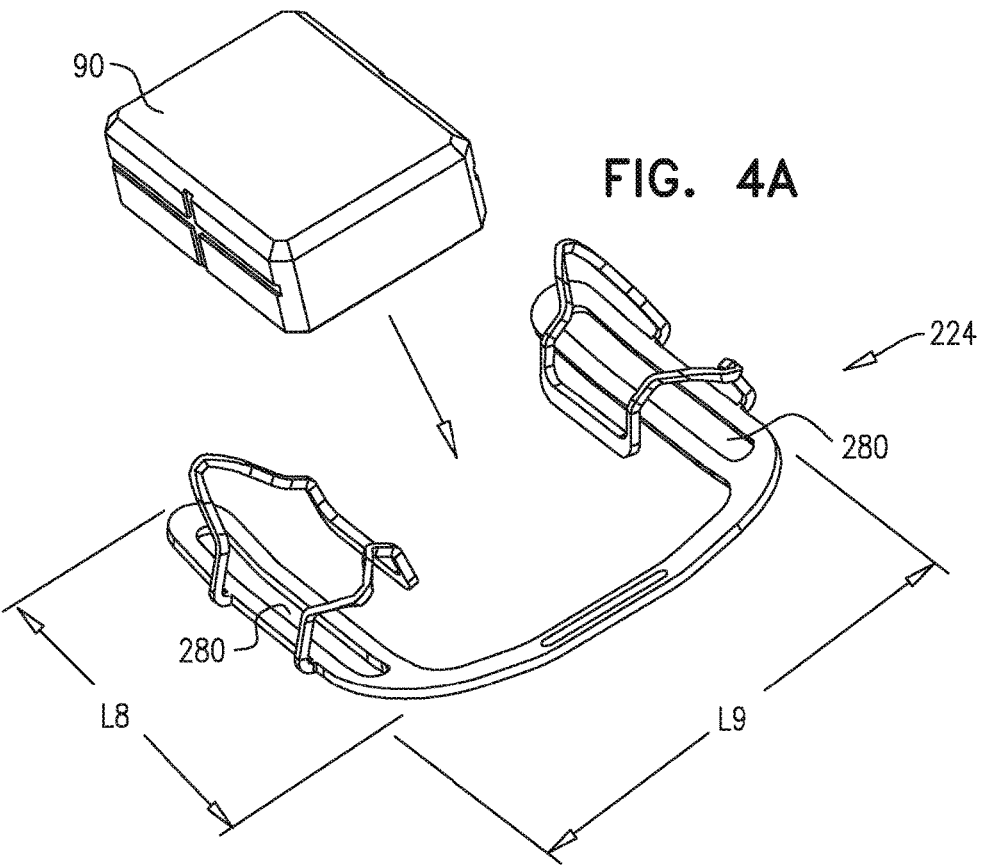
Figure 4B:
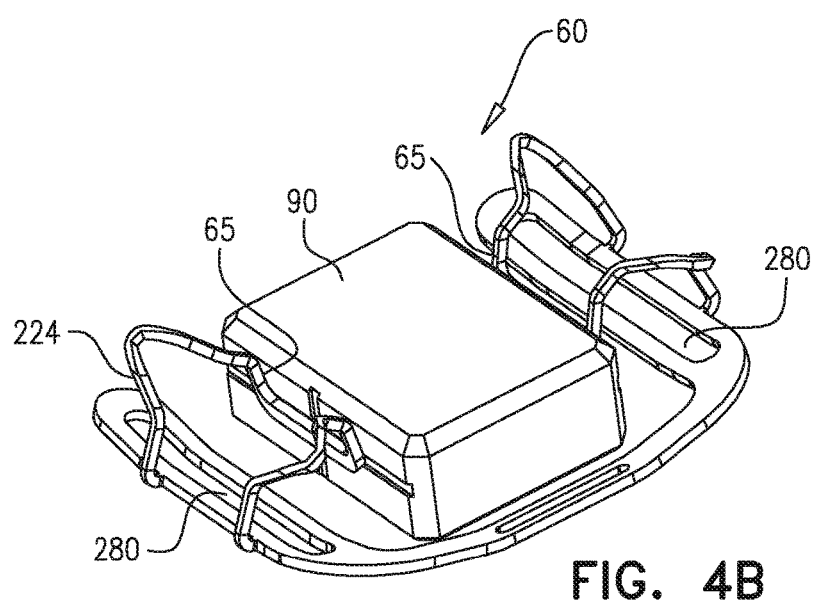
Figure 4C:
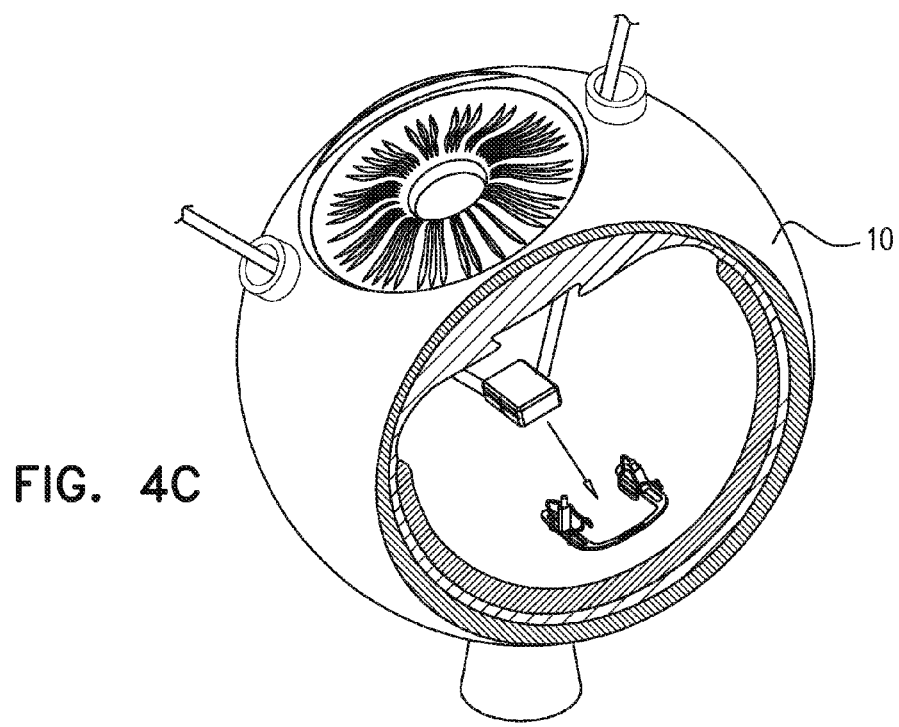

Reference is now made to FIGS. 4A-D which are schematic illustrations of apparatus 60 for implantation in an eye of a subject, in accordance with some applications of the present invention. Apparatus 60 typically comprises implantable retinal stimulator 90 configured for implantation on a retina of a subject's eye, and frame 224 which is shaped and sized to receive implantable retinal stimulator 90 and to surround stimulator 90 at least in part (as shown). Frame 224 is typically shaped to define at least one anchoring element receiving portion 280 which is configured to receive an anchoring element for securing implantable retinal stimulator 90 and frame 224 to retina 106. As shown in FIGS. 4A-C, frame 224 is shaped to define two, i.e., a first and a second, anchoring element receiving portions 280.

Typically, frame 224 has a length L8 in a first direction of 4-8 mm, and a length L9 of 5-11 mm in a second direction perpendicular to the first direction.

For some applications, frame 224 is shaped to define first and second guiding surfaces 65 extending away from element receiving portions 280. Typically, guiding surfaces 65 guide implantable retinal stimulator 90 into frame 224 such that stimulator 90 is positioned properly in frame 224 (analogously to an electric socket guiding the proper placement of an electric plug).

Figure 4D:
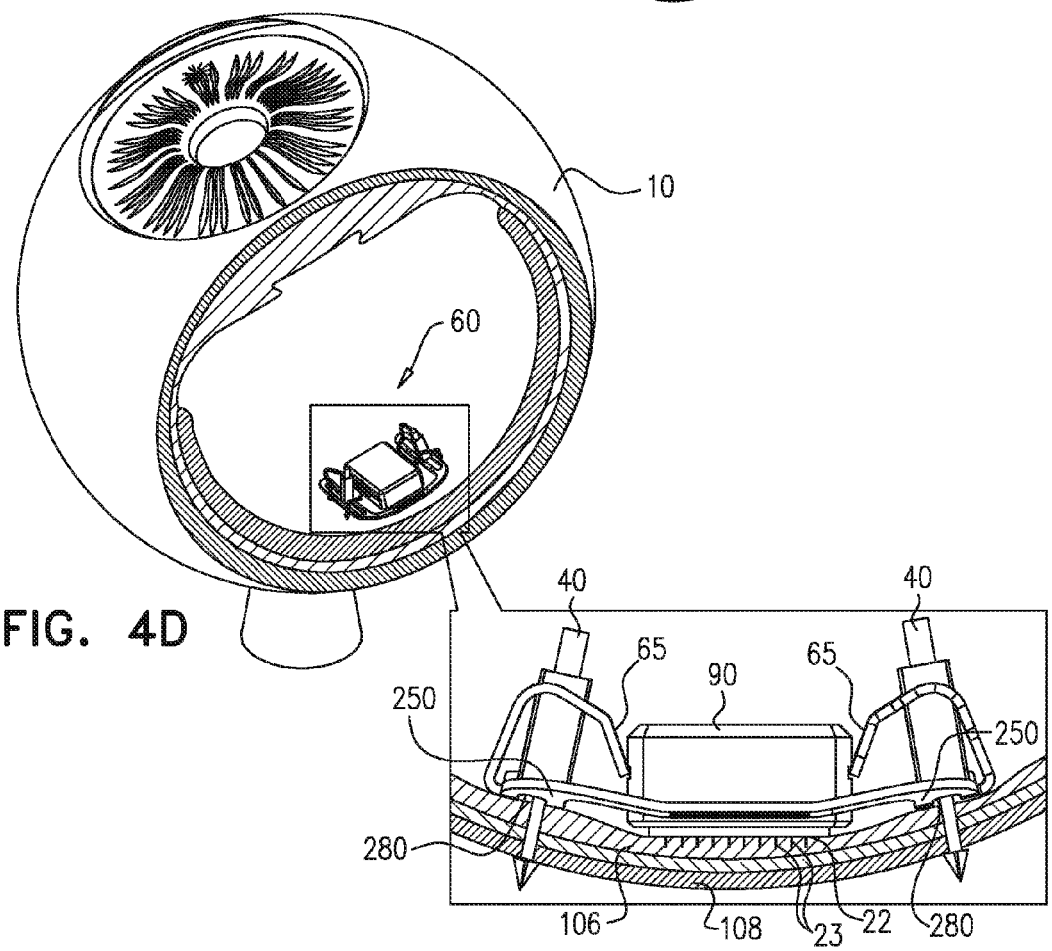

Anchoring element receiving portions 280 each comprise a tissue-contact surface 250 configured to contact a surface of retina 106 when apparatus 60 is implanted on the retina (FIG. 4D).

In accordance with some applications of the present invention, apparatus 60 further comprises at least one anchoring element 40, e.g., a tack, shaped and sized to be positioned in anchoring element receiving portion 280 and to penetrate scleral tissue 108. Anchoring element 40 secures apparatus 60 to the eye by penetrating tissue of the eye (e.g., sclera tissue).

Reference is still made to FIGS. 4A-C. Typically, during implantation of apparatus 60, frame 224 is positioned in an epi-retinal position on the retina. Frame 224 is typically inserted into the eye through an incision in a limbus or a pars plana of the eye. Frame 224 is typically inserted using a guide having an internal diameter of 1-4 mm, or through a cannula of 23 g-20 g placed in sclera 108 and having an internal diameter of 0.6-0.9 mm.

Subsequently to positioning frame 224 in an epi-retinal position on the retina, implantable retinal stimulator 90 is positioned in frame 224 (e.g., by snapping into guiding surfaces 65) such that frame 224 surrounds at least a portion of implantable retinal stimulator 90, and electrode array 22 penetrates retina 106.

Anchoring element 40 (as shown), or anchoring element 42 (not shown) is advanced into anchoring element receiving portion 280 such that the anchoring element penetrates scleral tissue 108 and secures stimulator 90 and frame 224 to the eye.

For some applications, anchoring element 40 is advanced into anchoring receiving element 280 subsequently to positioning of implantable retinal stimulator 90 in frame 224. Alternatively, anchoring element 40 is advanced into anchoring receiving element 280 subsequently to positioning frame 224 on the retina and prior to positioning of implantable retinal-stimulator 90 in frame 224.

For other applications, at least one anchoring element 40 is advanced into scleral tissue 108 prior to positioning frame 224 on the retina. Subsequently, frame 224 is positioned on the retina such that anchoring elements 40 are positioned in anchoring receiving elements 280. Stimulator 90 is then positioned in frame 224 such that electrode array 22 penetrates retina 106. Typically, a location on the retina is marked and anchoring element 40 is advanced into the marked location. For some applications, marking the location on the retina comprises puncturing the retina at the location. Alternatively, marking the location on the retina is done by applying light to the retina at the location. For example, laser light is applied to the location causing thereby denaturing of protein and marking the location by burning the tissue at the location. For some applications the light is applied to mark the location on the retina prior to, and while, the anchoring element is advanced.

Figure 4E:
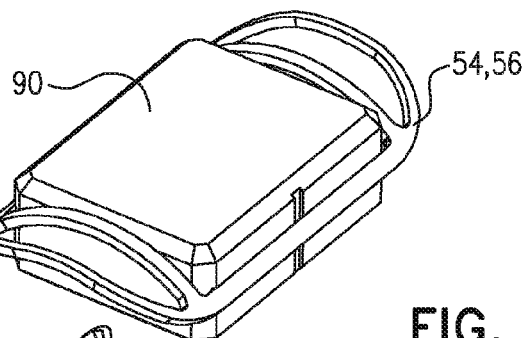
Figure 4F:
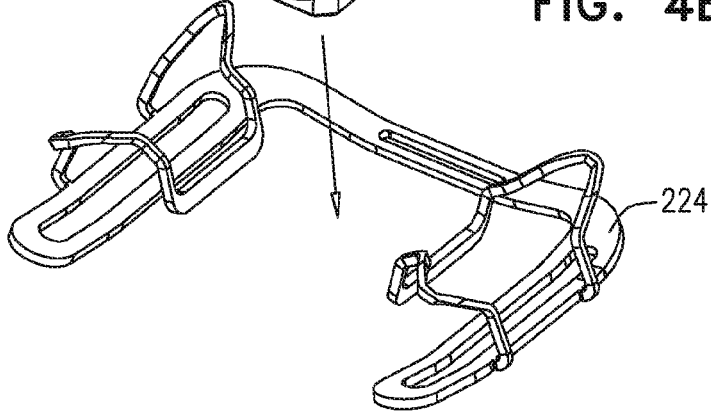
Figure 4G:
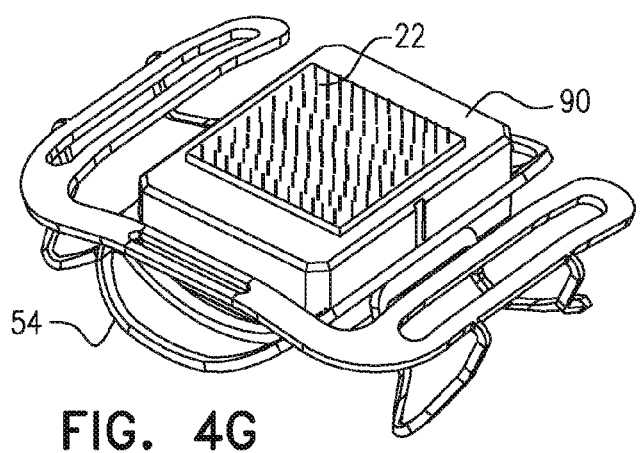

Reference is now made to FIGS. 4E-G. For some applications, implantable retinal stimulator 90 further comprises rim 54, which surrounds at least a portion of implantable retinal stimulator 90 (rim 54 being either an integral part of implantable retinal stimulator 90 or a separate rim which is coupled to implantable retinal stimulator 90). Rim 54 connects to, e.g., snaps into, frame 224 when stimulator 90 is positioned in frame 224.

Reference is now made to FIGS. 4H-I. For some applications, apparatus 60 comprises frame 223. Frame 223 is generally similar to frame 224 expect for as indicated otherwise. As shown in FIGS. 4H-I, frame 223 is shaped to define elevated guiding surfaces 165 extending away from anchoring element receiving portions 280 and shaped to define a bent portion 62. For such applications, interface member 56, e.g., rim 55, surrounds stimulator 90. As shown, rim 55 is shaped to define first and second windows 63. Implantable retinal stimulator 90 surrounded by rim 55 is positioned in frame 223 by being lowered into frame 223 such that, guiding surfaces 165 are inserted into windows 63 of rim 55. Rim 55 is pushed past bent portions 62 of guiding surface 165, such that rim 55 locks into guiding surfaces 165. Additionally or alternatively, anchoring element receiving portions 280 are shaped and sized such as to firmly surround the anchoring elements (not shown in FIGS. 4H-I) and reduce movement of frame 223 when the frame is fixed to the retina by anchoring elements 40. Typically, anchoring element receiving portions 280 of frame 223 has a length of 1.2-1.4 mm and a width of 0.5-0.6 mm.

Figure 5A:
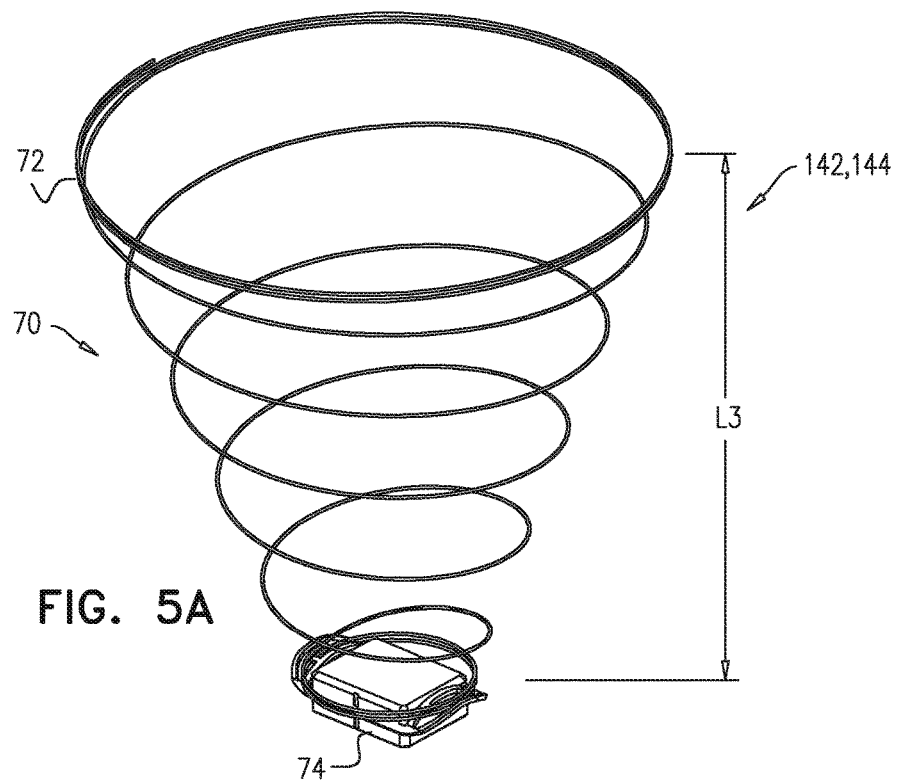
FIGS. 5A-B are schematic illustrations of apparatus for implantation in an eye of a subject, in accordance with some applications of the present invention.
Figure 5B:
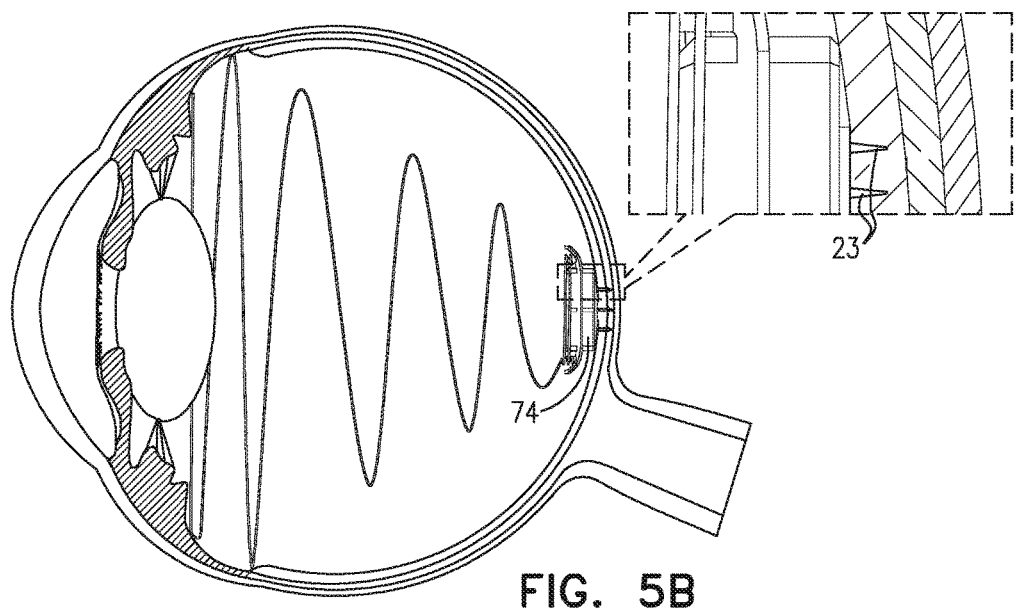

Reference is now made to FIGS. 5A-B, which are schematic illustrations of apparatus 70 for implantation in an eye of a subject, in accordance with some applications of the present invention. Apparatus 70 typically comprises implantable retinal stimulator 90 and an elastic anchoring element 142 coupled to implantable retinal stimulator 90. As shown in FIGS. 5A-B, for some applications, elastic anchoring element 142 is shaped to define an elastic conical helical anchor 144 coupled to implantable retinal stimulator 90 at a vertex of conical helical anchor 144 (it being appreciated that the vertex of conical helical anchor 144 has some non-zero size, and is not a strict geometrical vertex). Typically, a length L3 of conical helical anchor 144 is at least 1.3 and/or less than 2 cm, e.g., 1.5 cm It is noted that length L3 refers to the length of conical helical anchor 144 when unconstrained and having the helical shape as shown (i.e., length L3 does not refer to the length of a straight metal piece that forms conical helical anchor 144).

Elastic conical helical anchor 144 typically has a proximal end 72 and a distal end 74 (distal end 74 being at the vertex of conical helical anchor 144). Distal end 74 is coupled to implantable retinal stimulator 90. FIG. 5B shows apparatus 70 implanted in eye 10. As shown, apparatus 70 is deployed in eye 10 such that implantable retinal stimulator 90 is placed in contact with the retina. Electrode array 22 penetrates the retina whereas elastic conical helical anchor 144 does not penetrate the retina. Distal end 74 of anchor 144 is coupled to implantable retinal stimulator 90, but in contrast to array 22 of implantable retinal stimulator 90, distal end 74 does not penetrate eye tissue of the subject. Apparatus 70 is deployed in eye 10 such that proximal end 72 of elastic conical helical anchor 144 contacts an ora serrata of the eye, or a vicinity of the ora serrata within 4 mm of the ora serrata, when implantable retinal stimulator 90 is implanted on the retina.

It is noted with reference to FIGS. 5A-B that apparatus 70 is configured to be anchored to retina 106 without the use of tacks which penetrate scleral tissue.

Reference is now made to FIGS. 7A-C, which are different views of anchoring element 40 for use with apparatus and methods described herein for securing a retinal stimulator to the retina. Anchoring element 40 is typically shaped and sized to be advanced into scleral tissue of the subject to facilitate anchoring of a retinal prosthesis to the retina. Anchoring element 40 typically comprises a tissue penetrating portion 200, comprising (i) a cylindrical shaft 210, and (ii) a puncturing tip 220 disposed distal to cylindrical shaft 210. A length L4 of cylindrical shaft 210 is typically at least 0.4 mm and/or less than 1.2 mm. Typically cylindrical shaft 210 has a circular cross section. Anchoring element 40 additionally comprises a proximal portion 250, extending along a longitudinal axis A1 of anchoring element 40 and being proximal to tissue penetrating portion 200. Proximal portion 250 typically has a length L5 along longitudinal axis A1 that is at least 0.3 mm and/or less than 3 mm. As shown in FIGS. 7A-C, proximal portion 250 has a cross-sectional area, in a plane perpendicular to longitudinal axis A1 of anchoring element 40, that is greater than a cross-sectional area of cylindrical shaft 210, in a plane perpendicular to longitudinal axis A1 of anchoring element 40. Additionally, as shown, proximal portion 250 has a non-circular cross-sectional shape in a plane transverse to longitudinal axis A1. For example, the cross-section of proximal portion 250 in a plane perpendicular to longitudinal axis A1 of anchoring element 40 may have an oblong shape, e.g., a generally rectangular shape (for example, a rectangular shape with slightly curved edges (as shown in FIG. 7A) or corners). Typically, this cross-section of proximal portion 250 has a cross-sectional area of 0.5-3 mm2. Alternatively, proximal portion 250 has a circular cross-sectional shape.

Reference is again made to FIG. 1F showing use of anchoring element 40. As shown in FIG. 1F, anchoring element 40 is advanced into the eye of the subject and is positioned in anchoring element receiving portion 28 of frame 24 (frame 24 is coupled to implantable retinal stimulator 90). As shown, tissue penetrating portion 200 of anchoring element 40 passes through anchoring element receiving portion 28 to penetrate scleral tissue 108 of eye 10 in order to facilitate anchoring of apparatus 20 to the retina. In some cases, part of proximal portion 250 temporarily passes through anchoring element receiving portion 28 along with tissue penetrating portion 200. This typically happens when force is applied to anchoring element 40 that is not yet sufficient to cause tissue penetrating portion 200 to pass through scleral tissue 108 (the force being applied in a direction of longitudinal axis A1), even though the force is sufficient to deform scleral tissue 108. Length L5 of proximal portion 250 typically allows for some of portion 250 to temporarily pass through anchoring element receiving portion 28 during this pre-puncturing period. Typically, proximal portion 250 is long enough such that less than the entirety of proximal portion 250 passes through anchoring element receiving portion 28, thereby providing relative ease of withdrawing proximal portion 250 back through anchoring element receiving portion 28 following the actual puncturing of scleral tissue 108. Once tissue penetrating portion 200 is disposed in scleral tissue 108, proximal portion 250 is pulled back through anchoring element receiving portion 28. Anchoring element 40 is then typically rotated, thereby locking anchoring element 40 to frame 24 such that proximal portion 250 of anchoring element 40 does not pass through anchoring element receiving portion 28 and does not penetrate the retina. As shown, the non-circular cross-sectional shape of proximal portion 250 of element 40 allows proximal section 250 to remain above the retina when anchoring element 40 is rotated to a locked position (FIG. 1F) in anchoring element receiving portion 28.

Reference is now made to FIGS. 6A-C which are different views of anchoring element 42 for use with apparatus and methods described herein for securing a retinal prosthesis to the retina. Anchoring element 42 is generally the same as anchoring element 40 except for differences described hereinbelow.

Similar to anchoring element 40, anchoring element 42 is shaped to define tissue penetrating portion 200, comprising cylindrical shaft 210, and puncturing tip 220 disposed distal to cylindrical shaft 210. Anchoring element 42 additionally comprises a proximal portion 252, extending along a longitudinal axis A1 of anchoring element 42 and being proximal to tissue penetrating portion 200.

Proximal portion 252 comprises a proximal element 251 and a distal element 253. Proximal portion 252 is shaped to define a recess portion 260 between proximal element 251 and distal element 253. A distance D1 between proximal element 251 and distal element 253 is typically at least 75 microns and/or less than 175 microns.

Figure 8A:
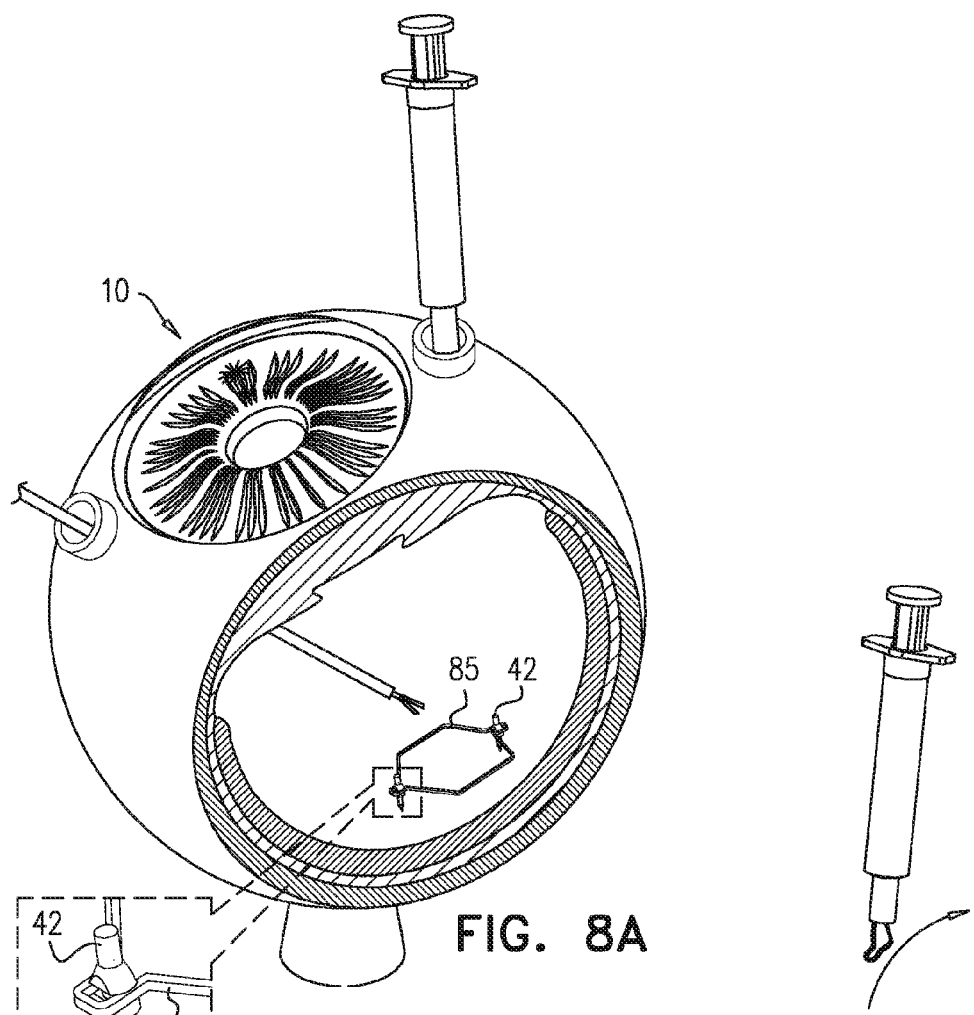
FIGS. 8A-C are schematic illustrations of a guide template for use with the apparatus for implantation in an eye of a subject, in accordance with some applications of the present invention.
Figure 8B:
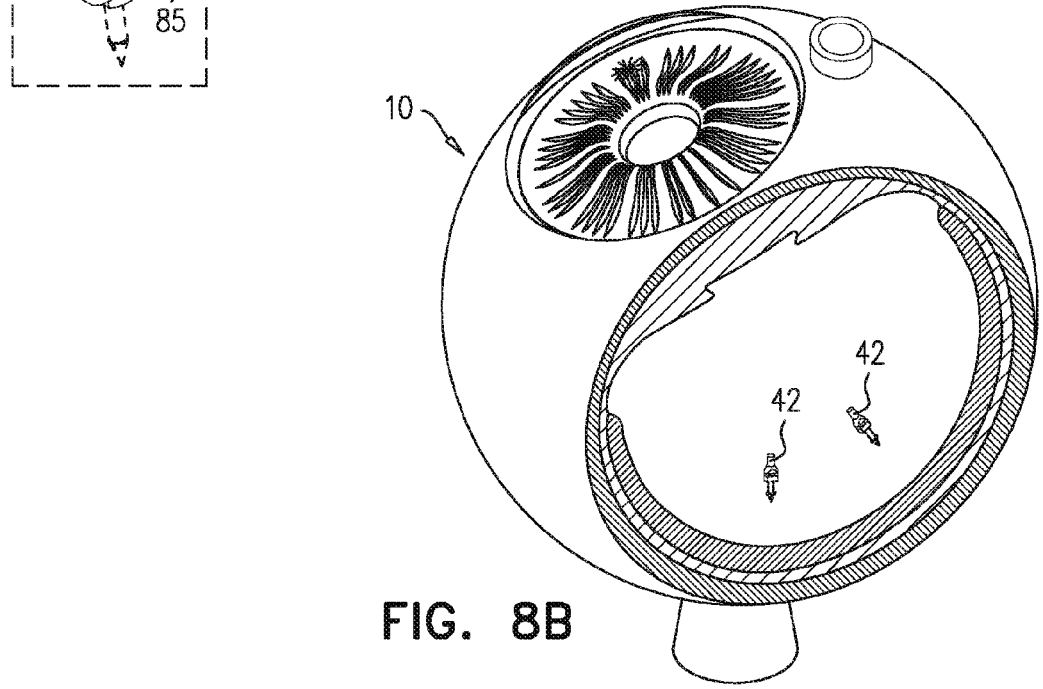
Figure 8C:
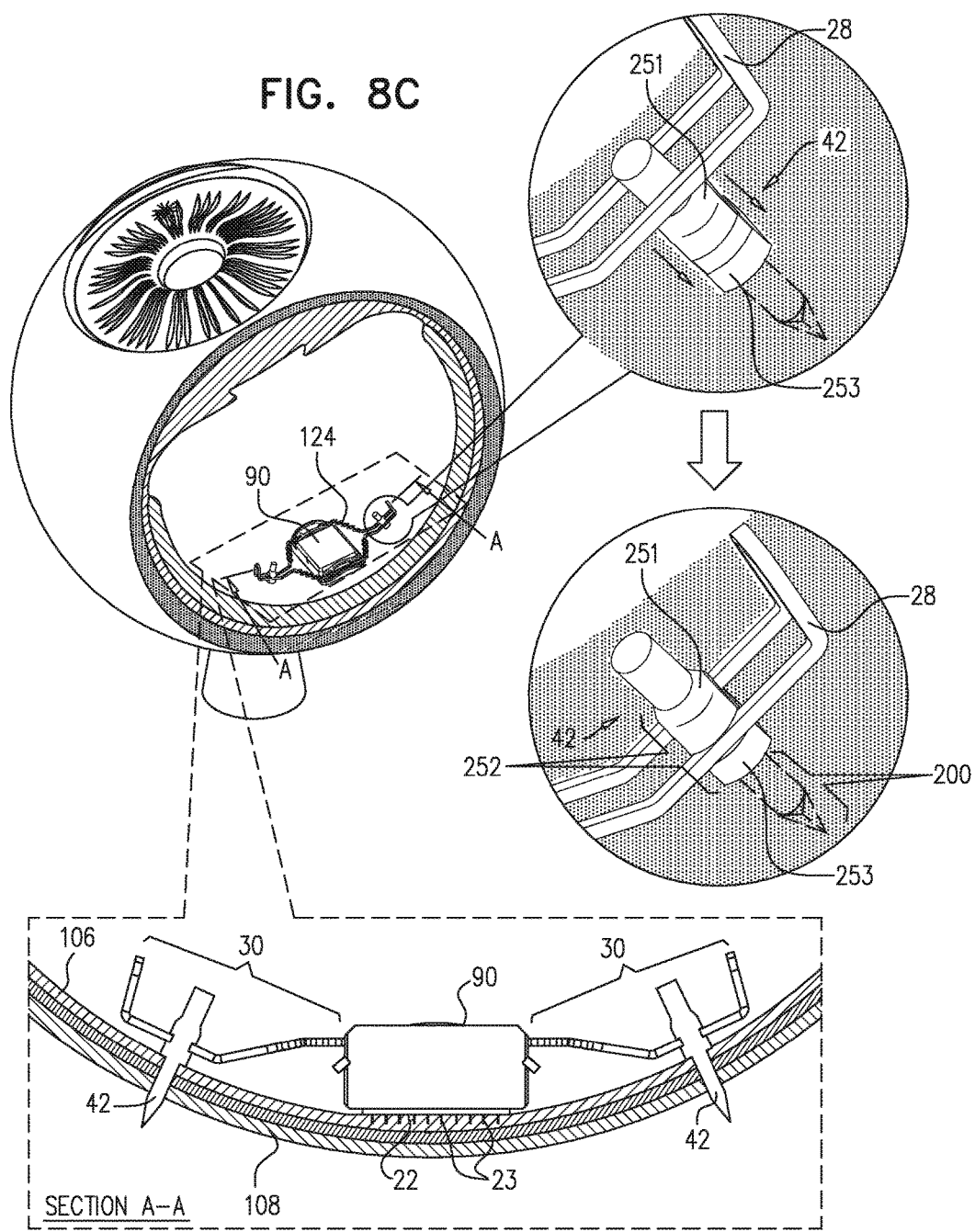

Anchoring element 42 is described hereinbelow with reference to FIGS. 8A-C. As shown in FIGS. 8A-C, anchoring element 42 is typically used for applications in which the anchoring element. 42 is positioned prior to positioning of an implantable retinal stimulator 90 and prior to positioning of a frame (24, 124, 224).

Reference is now made to FIGS. 8A-C. As shown in FIG. 8A, for some applications, a guide template 85 is used to mark a location for implantation of anchoring elements 42. Typically, guide template 85 is used in cases in which anchoring elements 42 are positioned prior to positioning of an implantable retinal stimulator 90 and prior to positioning of a frame (24, 124, 224). Once both anchoring elements 42 are properly positioned, guide template 85 is typically removed from the eye (FIG. 8B). For some applications, guide template 85 remains in the eye during placement of implantable retinal stimulator 90 (e.g., to guide the placement of implantable retinal stimulator 90), and is then removed, or guide template 85 chronically remains in the eye.

As shown in FIG. 8C, an assembly of frame 124 secured to rim 54, which in turn surrounds implantable retinal stimulator 90 (as shown in FIGS. 3A-B) is advanced into eye 10 and positioned in an epi-retinal position such that array 22 penetrates retina 106 and anchoring element receiving portions 28 of frame 124 are snapped onto anchoring elements 42. As shown, distal portion 200 of anchor 42 penetrates scleral tissue 108. Also as shown, proximal portion 252 of anchoring element 42 engages anchoring element receiving portion 28 such that proximal element 251 is positioned above anchoring element receiving portion 28, and distal portion 253 is positioned below anchoring element receiving portion 28. As shown in FIG. 8C, proximal portion 252 of anchoring element 42 does not penetrate the retina. As shown in FIG. 8C, element receiving portion 28 of frame 124 remains above retina 106 when using anchoring element 42.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. Apparatus, comprising:
an implantable retinal stimulator, configured for implantation on a retina of a subject's eye, and comprising (i) an electrode array comprising electrodes; (ii) a plurality of photosensors; and (iii) driving circuitry, configured to drive the electrodes to apply currents to the retina;
an interface member disposed at an outer surface of the implantable retinal stimulator;
a frame, (i) physically separated from the interface member, (ii) shaped and sized to intraocularly become coupled to the interface member and to surround the implantable retinal stimulator at least in part, and (iii) shaped to define at least a first anchoring element receiving portion; and an anchoring element shaped and sized to be positioned in the anchoring element receiving portion and to penetrate scleral tissue of the subject, wherein the frame is shaped to define at least a first extension portion, the first extension portion shaped to define the at least one anchoring element receiving portion, and wherein the frame is shaped to define a second extension portion, opposite the first extension portion, and shaped to define a second anchoring element receiving portion.

2. The apparatus according to claim 1, wherein the first and second extension portions are each geometrically shaped to increase flexibility of the first and second extension portions versus if the first and second extension portions were straight.

3. The apparatus according to claim 2, wherein the first and second extension portions are each shaped at least in part as a shape selected from the group consisting of: a repeating wave pattern and an undulating pattern.

4. The apparatus according to claim 1, wherein the first anchoring element receiving portion is not parallel to the second anchoring element receiving portion when the first and second anchoring element receiving portions are unconstrained.

5. The apparatus according to claim 1, wherein the frame is shaped to define first and second guiding surfaces extending away from the first and second anchoring element receiving portions, and configured to guide the implantable retinal stimulator into the frame.

6. The apparatus according to claim 5, wherein the interface member is shaped to define a first and a second window, and wherein the first and second guiding surfaces are configured to guide the implantable retinal stimulator into the frame by the first and second guiding surfaces being inserted into the first and second windows.

7. Apparatus, comprising:
an implantable retinal stimulator, configured for implantation on a retina of a subject's eye, and comprising (i) an electrode array comprising electrodes; (ii) a plurality of photosensors; and (iii) driving circuitry, configured to drive the electrodes to apply currents to the retina;
an interface member disposed at an outer surface of the implantable retinal stimulator;
a frame, (i) physically separated from the interface member, (ii) shaped and sized to intraocularly become coupled to the interface member and to surround the implantable retinal stimulator at least in part, and (iii) shaped to define at least a first anchoring element receiving portion;
an anchoring element shaped and sized to be positioned in the anchoring element receiving portion and to penetrate scleral tissue of the subject; and
an implantation needle, wherein the frame is shaped and sized to be deployed through the implantation needle.

8. The apparatus according to claim 7, wherein the frame is shaped to define at least a first extension portion, the first extension portion shaped to define the at least one anchoring element receiving portion.

9. The apparatus according to claim 8, wherein the frame is shaped to define a second extension portion, opposite the first extension portion, and shaped to define a second anchoring element receiving portion.

10. Apparatus, comprising:
an implantable retinal stimulator, configured for implantation on a retina of a subject's eye, and comprising (i) an electrode array comprising electrodes; (ii) a plurality of photosensors; and (iii) driving circuitry, configured to drive the electrodes to apply currents to the retina;
a frame, (i) physically separated from the implantable retinal stimulator, (ii) shaped and sized to intraocularly become coupled to the implantable retinal stimulator and to surround the implantable retinal stimulator at least in part, and (iii) shaped to define at least one anchoring element receiving portion; and
an anchoring element shaped and sized to be positioned in the at least one anchoring element receiving portion and to penetrate scleral tissue of the subject,
wherein the frame is shaped to define at least a first extension portion, the first extension portion shaped to define the at least one anchoring element receiving portion, and wherein the frame is shaped to define a second extension portion, opposite the first extension portion, and shaped to define a second anchoring element receiving portion.

11. The apparatus according to claim 10, wherein the frame has a length of 6-15 mm.

12. The apparatus according to claim 10, wherein the frame is (a) shaped to define first and second guiding surfaces extending away from the first and second anchoring element receiving portions, and (b) configured to guide the implantable retinal stimulator into the frame.

13. The apparatus according to claim 10, wherein the first and second extension portions are each geometrically shaped to increase flexibility of the first and second extension portions versus if the first and second extension portions were straight.

14. The apparatus according to claim 10, wherein the first and second anchoring element receiving portions each comprise a tissue-contact surface configured to contact a surface of the retina when the apparatus is implanted on the retina.

15. The apparatus according to claim 10, wherein the first anchoring element receiving portion is not parallel to the second anchoring element receiving portion when the first and second anchoring element receiving portions are unconstrained.

16. The apparatus according to claim 10, wherein the anchoring element comprises:
a tissue penetrating portion, comprising (i) a cylindrical shaft 0.4-1.2 mm in length, and (ii) a puncturing tip and disposed distal to the cylindrical shaft; and
a proximal portion, 1.5-3 mm in length, extending along a longitudinal axis of the anchoring element, proximal to the tissue penetrating portion, and having:
(i) a cross-sectional area, in a plane perpendicular to the longitudinal axis of the anchoring element, that is greater than a cross-sectional area of the cylindrical shaft, in a plane perpendicular to the longitudinal axis of the anchoring element, and
(ii) a non-circular cross-sectional shape in a plane transverse to the longitudinal axis.

* * * * *